(12) United States Patent
Akiyoshi et al.

(10) Patent No.: US 9,523,082 B2
(45) Date of Patent: Dec. 20, 2016

(54) FIREFLY LUCIFERASE

(71) Applicants: OLYMPUS CORPORATION, Tokyo (JP); NIMURA GENETIC SOLUTIONS CO., LTD., Tokyo (JP); PERAK STATE DEVELOPMENT CORPORATION, Perak Darul Ridzuan (MY)

(72) Inventors: Ryutaro Akiyoshi, Hachioji (JP); Katsunori Ogo, Hachioji (JP); Hirobumi Suzuki, Hino (JP)

(73) Assignees: OLYMPUS CORPORATION, Tokyo (JP); NIMURA GENETIC SOLUTIONS CO., LTD., Tokyo (JP); PERAK STATE DEVELOPMENT CORPORATION, Perak Darul Ridzuan (MY)

( * ) Notice: Subject to any disclaimer, the term of this patent is extended or adjusted under 35 U.S.C. 154(b) by 0 days.

(21) Appl. No.: 14/250,866

(22) Filed: Apr. 11, 2014

(65) Prior Publication Data
US 2015/0291938 A1    Oct. 15, 2015

(51) Int. Cl.
*C12N 9/02* (2006.01)
*C12Q 1/66* (2006.01)

(52) U.S. Cl.
CPC .............. *C12N 9/0069* (2013.01); *C12Q 1/66* (2013.01); *C12Y 113/12007* (2013.01)

(58) Field of Classification Search
CPC combination set(s) only.
See application file for complete search history.

(56) References Cited

FOREIGN PATENT DOCUMENTS

| JP | 2006-301599 A | 11/2006 |
| WO | WO 2006/088109 A1 | 8/2006 |

OTHER PUBLICATIONS

Kim et al. (2004) Eur. J. Entomol. 101: 1-11.*
Hou et al. "Molecular cloning, expression and sequence analysis of luciferase RT from Luciola terminals." Submitted (Nov. 2007) to the EMBL/GenBanl/DDBJ databases UniProt B3TMS5_9COLE.*
Isobe et al. (Pure and Appl. chem. 70(11): 2085-92.*

* cited by examiner

*Primary Examiner* — Lisa J Hobbs
(74) *Attorney, Agent, or Firm* — Scully, Scott, Murphy & Presser, P.C.

(57) ABSTRACT

The present invention relates to a luciferase derived from a Malaysian *Luciola* firefly, the luciferase having a maximum luminescent wavelength of 557 nm at pH 8, or the luciferase inducing luminescence having 1.5 times or more the luminous intensity of luminescence induced by *Photinus pyralis* firefly luciferase.

3 Claims, 3 Drawing Sheets

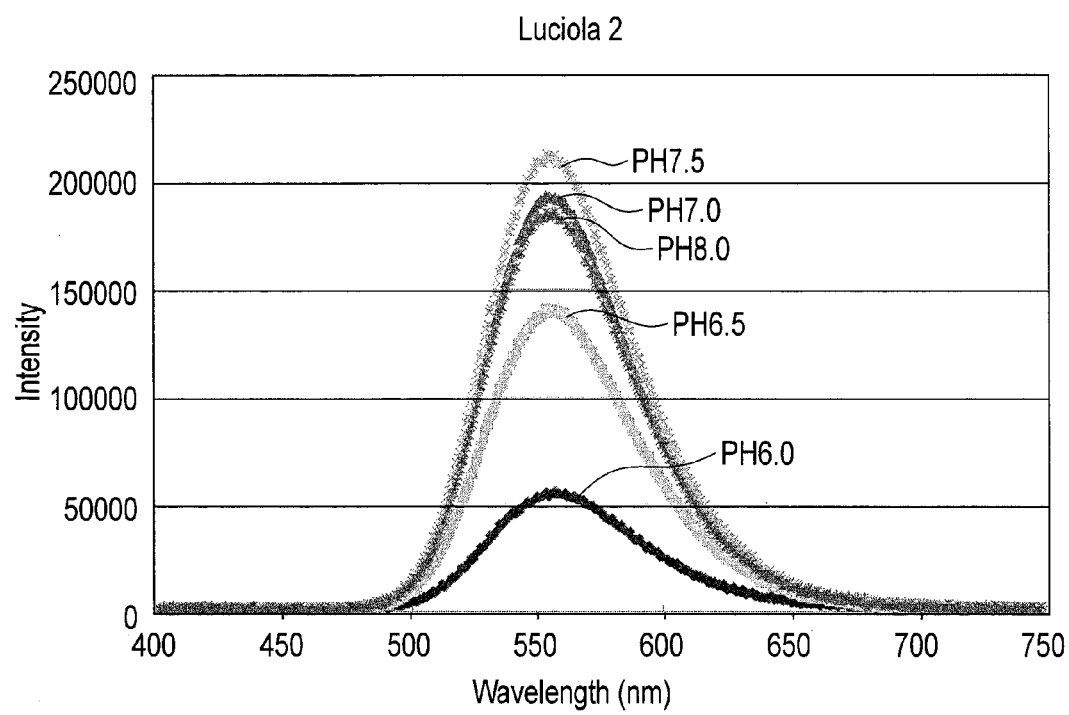
F I G. 1
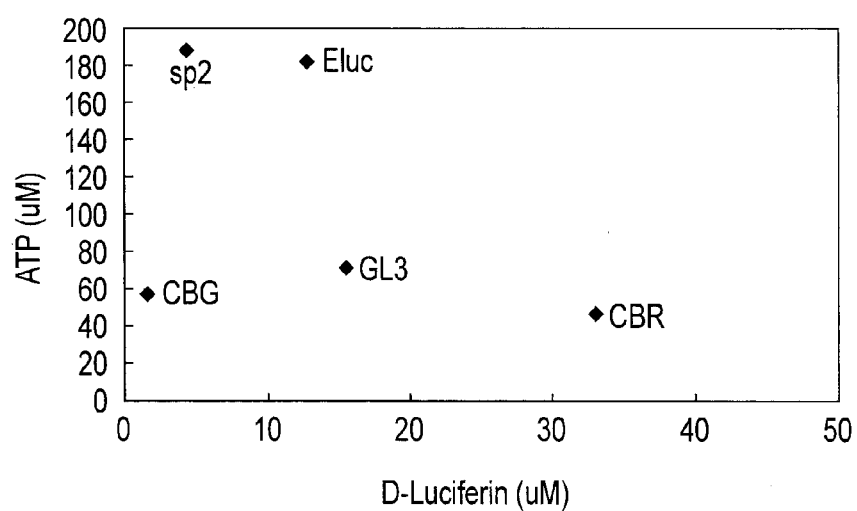
F I G. 2

FIREFLY LUCIFERASE

BACKGROUND OF THE INVENTION

The present invention relates to a firefly luciferase. More specifically, it relates to a firefly luciferase which emits light at high luminosity, the variants thereof, and a method for determining function of a cell by expressing a gene of the luciferase in a cell and detecting the light emission by means of imaging.

For determining function of cells such as intracellular signal transduction and gene expression, a fluorescent probe such as a fluorescent dye and fluorescent protein and a luminescent probe utilizing luciferine-luciferase reaction have been used. Especially, for the analysis of gene expression regulation, luminescence measurement which does not cause damage of cell due to exciton light or autofluorescence and is excellent in terms of quantitative determination is used. For example, in the case of observing a cell to which a luciferase gene is introduced, the intensity of expression of the luciferase gene (more specifically, the expression amount) can be determined by measurement of the luminescence from the cell by luciferase. The measurement of the luminescence is performed by the procedures in which luciferine, ATP, and the like are added to a lysate prepared by lysis of cells, and the solution is subjected to a quantitative determination by a luminometer utilizing a photoelectric multiplier. Namely, the degree of luminescence is measured after lysis of cells, and thus the expression amount of luciferase gene at a certain time point is determined as an average value of the entire cell. Examples of a method for introducing a luminescence gene such as luciferase gene as a reporter gene are a calcium phosphate method, lipofection, and electroporation, and each of these methods is used in accordance with the purpose and type of cells. Analysis of the expression amount of luciferase with use of an objective DNA fragment ligated to the upstream or downstream of luciferase gene to be introduced into a cell enables study of the effect of the DNA fragment on transcription of luciferase gene. Further, co-expression of luciferase gene to be introduced into a cell and the objective gene enables study of the effect of the gene product on expression of a luciferase gene.

For time-course analysis of the expression amount of a luminescence gene, the degree of luminescence of a living cell needs to be measured over time. Such measurement is carried out by cell cultivation in an incubator provided with a luminometer and quantitative determination of the degree of luminescence from the whole cell population for a given length of time. In this way, an expression rhythm etc. having a certain cycle can be analyzed, and the time course of the expression amount of the luminescence gene in the entire cell can be obtained.

In recent years, in biology and medical science fields there is increasing necessity of the time course observation of dynamic alterations in living samples with images. In a field of utilizing observation of fluorescence, time lapse or dynamic image pickup has been adopted for dynamically understanding function of a protein molecular. In the conventional technique, time course observation with use of a fluorescent sample has been carried out, for example, observation of moving images for one molecule of a protein provided with an added fluorescent molecule.

In contrast, when a luminescent sample is used for time-course observation, a CCD camera equipped with an image intensifier is required since the luminous intensity of the luminescent sample is extremely low. Recently, a microscope equipped with an optical system for observation of luminescent samples has been developed (Jpn. Pat. Appln. KOKAI Publication No. 2006-301599, International Publication No. 2006/088109).

Upon image pickup of a luminescent sample having small luminous intensity, it should be exposed for a longer term for obtaining clear image. Such a luminescent sample is used for only limited research. For example, when 30 minutes of exposure is required because of low luminous intensity, time-course image pickup is possible at every 30 minutes but is not at a shorter time, and real-time image pickup is also impossible. Plural images should be obtained and compared in order to focus on cells which emit light, and thus when longer exposure time is required because of low luminous intensity, it is time-consuming.

BRIEF SUMMARY OF THE INVENTION

The object of the present invention is provision of luciferase inducing high luminescence in comparison to the conventional firefly luciferase.

A luciferase of a first aspect is characterized by being derived from Malaysian fireflies belonging to genus *Luciola*.

A luciferase of a second aspect induces luminescence such that a maximum luminous wavelength is 557 nm at pH 8.

A luciferase of a third aspect induces luminescence such that a maximum luminous wavelength falls within a range of 555 to 560 nm over the entire pH range of 5.5 to 8.0.

A luciferase of a fourth aspect induces luminescence having 1.5 times or more the luminous intensity of luminescence induced by *Photinus pyralis* (hereinafter, referred to as *P. pyralis*) firefly luciferase.

According to one embodiment, a luciferase inducing luminescence having higher luminous intensity than that of conventional firefly luciferase is provided, and thus luminescence can be detected even with a minute amount of luciferase, thereby the exposure time necessary for luminescent image pickup can be shorten and the time-course observation with higher time resolution can be achieved compared to that of the conventional technique.

BRIEF DESCRIPTION OF THE SEVERAL VIEWS OF DRAWINGS

FIG. 1 shows luminescent spectra of SP2 luciferase at various pHs.

FIG. 2 illustrates Km values with respect to various luciferases.

Figure 3:
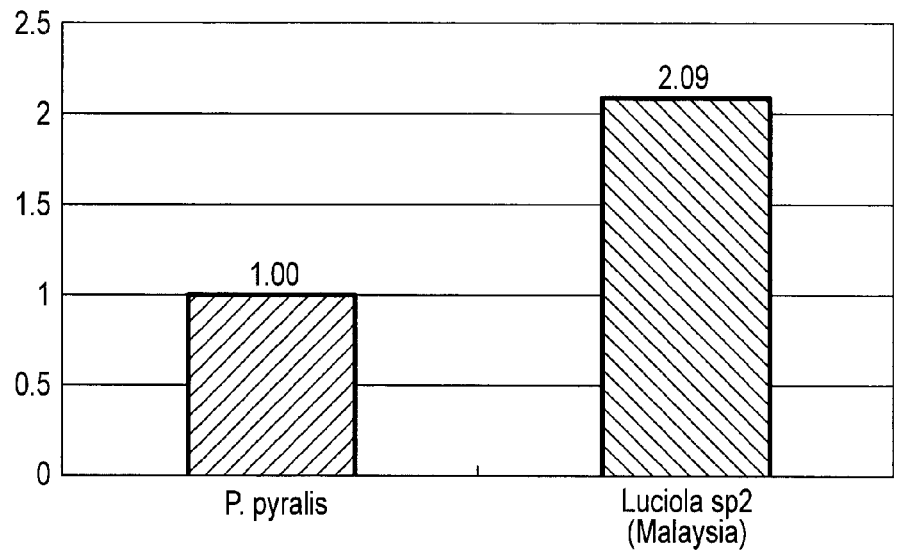

FIG. 3 compares SP2 and *P. pyralis* luciferases expressed in a mammal cell with respect to luminous intensity.

Figure 4:
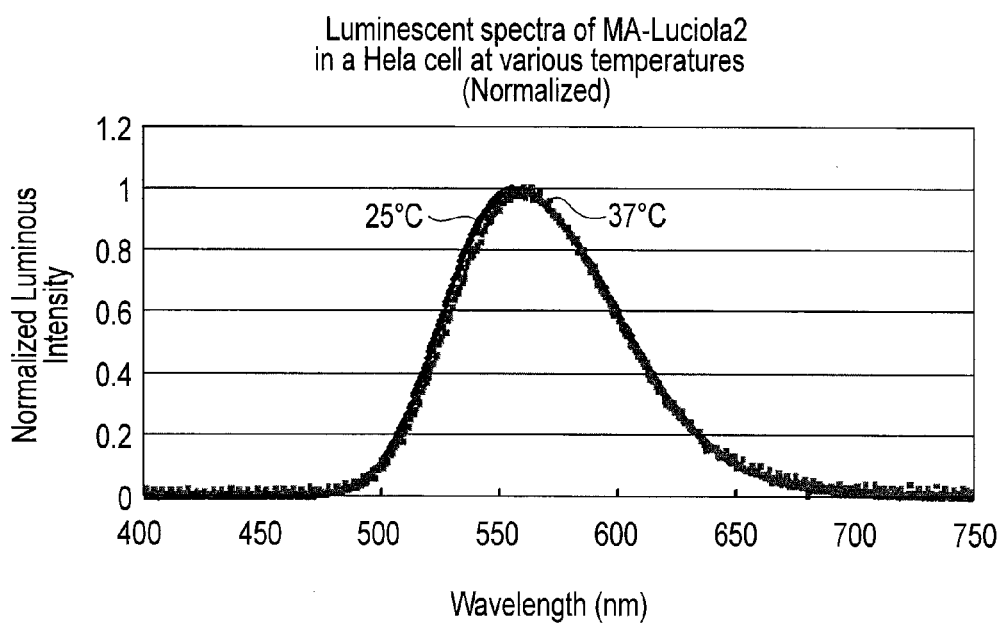

FIG. 4 shows luminescent spectra of SP2 luciferase at various temperatures (25 and 37° C.).

Figure 5:
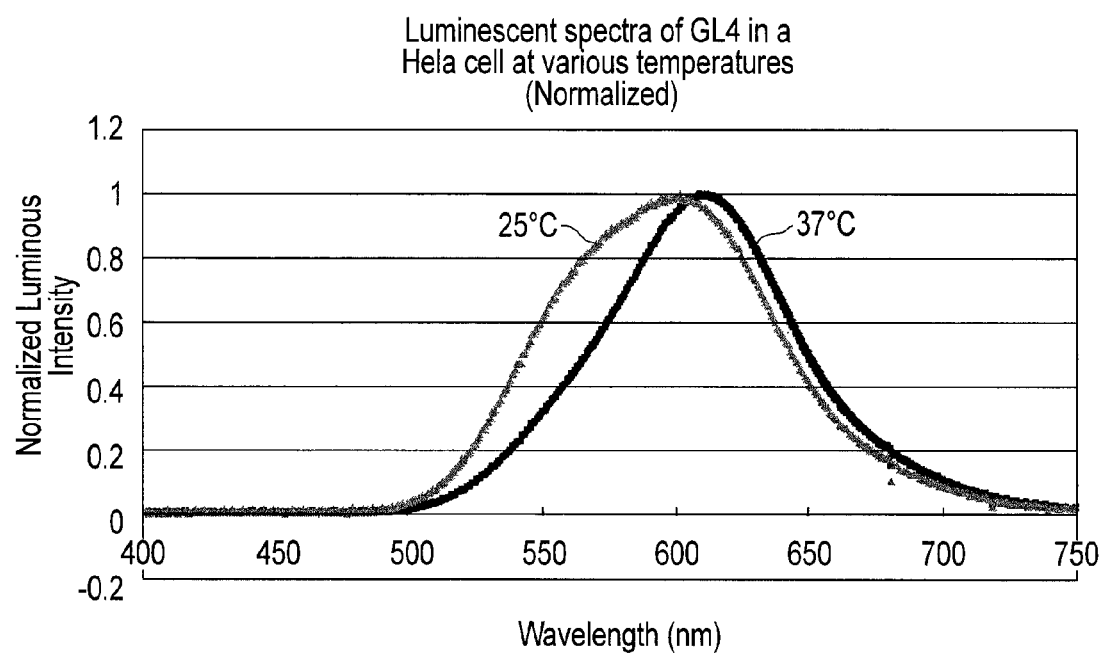

FIG. 5 shows luminescent spectra of *P. pyralis* luciferase expressed in a mammal cell at various temperatures (25 and 37° C.).

DETAILED DESCRIPTION OF THE INVENTION

The present invention relates to a luciferase derived from a Malaysian *Luciola* firefly.

"Luciferase" is a class of enzyme which catalyzes a luminescent chemical reaction. The substrate of this enzyme is called as luciferin. In the presence of ATP, emission of light occurs upon chemical reaction of luciferin because of a catalytic activity of luciferase. Presently, luciferases derived from fireflies and bacteria have been obtained. The luciferase of an embodiment also indicates those defined above, but is novel one which has been first obtained from the firefly described below.

The luciferase is derived from a Malaysian firefly belonging to the genus *Luciola*. The fireflies are native mainly to Malaysia, and include those which have been only proved to belong to the genus *Luciola*, although a scientific name has not yet been assigned. Here, the term "derive" means to include not only wild-type luciferases from the Malaysian *Luciola* firefly but also mutants thereof.

The luciferase indicates remarkably high luminous intensity in comparison to known luciferases. Thus, the luciferase exhibits a particularly advantageous effect when it is used as a reporter for imaging of a protein. More specifically, the luciferase enables excellent detection of a protein whose expression amount is small since it can provide a high degree of luminescence even with a small amount. The luciferase is capable of reducing the exposure time which is necessary for detection, because of high luminous intensity. Therefore, it enables the reduction of the time of image pickup by utilizing the luciferase of the present invention as a reporter for time-course observation, thereby achieving observation which is closer to real-time observation.

An example of the luciferase is those including the amino acid sequence represented by SEQ ID NO: 1. The amino acid sequence of SEQ ID NO: 1 is:

MNKNIIYGPPPVYPLDDGTGGEQLYKCILRYAKIPECVALTSAHTKESIL

YEELLQLTCKLAQSLKRCGITRNSTIAVCSENNLQYFIPIIAGLYIGAAT

AAVNNRYNERELTDILNLSKPDIIFCSKETLPKICQVKKKLNYIKEIIVL

DSKHDSELAQCLDNFISHNCNKDFDAYQFKPSSFNRNEQVGLILNSSGST

GLPKGVMLTHKNLVVRFSHCKDPVFGNIISPGTAILTVIPFHHGFGMFTT

LGYFTCGFRIVLMHTFYEKLFLQALEDYKVESTLLVPTLMTFFAKSALVD

KYNLPYLKEIASGGAPLSKEIGEAVARRFKLNAIRQGYGLTETTSAVLIT

PESETVPGSIGKVVPFFAAKIIDHRTGKALGPNEVGELCFKGDMIMKGYC

NNIEATNAIIDNDGWLHSGDLGYYNDDKHFFIVDRLKSIIKYKGYQVAPA

ELEGILLTHPSIMDAGVTGIPDDNAGELPAACVVVKPGRHLTEENVINYV

SSQVSSVKRLRGGVRFLDEIPKGSTGKIDTTALKQILQKPNCKL*.

The luciferase has been obtained from a firefly inhabiting mainly in Malaysia for which a scientific name has not been assigned although it has been proved to belong to the genus *Luciola*. In the disclosure, the fireflies are referred to as *Luciola* sp2 or as sp2, and the luciferase derived from the fireflies is referred to as SP2 luciferase.

A luciferase of an embodiment of the present invention has a characteristic of inducing luminescence such that change of a maximum luminous wavelength is small when pH varies. Here, "maximum luminous wavelength" means a wavelength at which intensity of luminescence is the maximum within a measurement wavelength range in a luminous reaction in which a luciferase is involved. With use of the luciferase a measurement or observation can be carried out, reducing an environmental pH influence. For example, with respect to luminescence induced by luciferases which are present in an environment of different pHs, luminous intensities can be measured at a single wavelength at the same time in an imaging by microscope. According to the luciferase of an embodiment of the present invention, quantitative measurement can be facilitated even with use of an apparatus in which photoelectric conversion efficiency varies depending on the measurement wavelength, for example, CCD. When a measurement is carried out with use of a conventional luciferase, the measurement wavelength needs be adjusted for each pH, which makes quantitative comparison difficult due to the difference of measurement wavelength. In contrast, when a measurement is carried out with use of a luciferase of an embodiment of the present invention, a single measurement wavelength can be used, thereby making quantitative comparison easier.

A luciferase of an embodiment of the present invention is characterized by inducing luminescence such that a maximum luminous wavelength falls within a certain range over a certain pH range. For example, a luciferase of an embodiment of the present invention induces luminescence such that a maximum luminous wavelength falls within a range of 520-600 nm, 530-590 nm, 540-580 nm, 545-575 nm, 550-570 nm, 553-565 nm or 555-560 nm over the entire range of pH 6.5-7.0, pH 6.0-7.5, pH 5.5-8.0, pH 5.0-8.5 or pH 4.5-9.0.

In FIG. 3, luminous intensity of SP2 luciferase is compared to that of *P. pylaris* luciferase. This figure indicates that SP2 luciferase has 1.8 times or more of luminous intensity in comparison to that of *P. pylaris*. As is shown by the figure, the luciferase has higher luminous intensity in comparison to a conventional firefly luciferase of *P. pyralis*. For example, the luciferase of the embodiment can induce luminescence having 1.2 times or more, 1.5 times or more, 1.8 times or more, 2.0 times or more the luminous intensity of that induced by *P. pyralis*.

A luciferase of an embodiment of the present invention includes not only those of wild type which is derived from Malaysian *Luciola* fireflies, but also mutant luciferases in which a part of the amino acid sequence of wild-type luciferase is mutated. Such mutation may be those which improve the enzymatic activity thereof. Here, the mutant luciferase may be those containing mutations in the amino acid sequence, for example, substitution, deletion, and/or addition of amino acids, as long as it indicates the characteristics of the luciferase of the present invention, that is, higher luminous intensity in comparison to conventional luciferases. The mutation is those of at least one of amino acid of the wild-type luciferase amino acid sequence, and preferably those of 1 to 130, 1 to 100, 1 to 80, 1 to 60, 1 to 40, 1 to 20, 1 to 15, 1 to 10, or 1 to 5 amino acids of the wild-type luciferase. Preferably, amino acid sequence of mutant luciferases has homology of 75% or more, 80% or more, 85% or more, 90% or more, 95% or more, 96% or more, 97% or more, 98% or more, or 99% or more with amino acid sequence of the wild-type luciferase. The mutation can be caused due to addition of Kozak sequence which is explained below. For example, the luciferase of the embodiment is a luciferase represented by SEQ ID NO: 30. The luciferase represented by SEQ ID NO: 30 is a luciferase obtained by adding Kozak sequence and introducing a mutation of N2D into the amino acid sequence represented by SEQ ID NO: 1. More specifically, asparagine at position 2 in the sequence is substituted by aspartate.

The present invention relates to a nucleic acid including the base sequence encoding the luciferase of the present invention. Namely, the nucleic acid includes luciferase gene which is derived from a Malaysian *Luciola* firefly. In the present invention, a nucleic acid indicates, for example, DNA or RNA. In the present invention, a "gene" of luciferase means mainly a region transcribed by mRNA, that is, a structural gene.

An example of a nucleic acid containing base sequence encoding the luciferase of an embodiment is a nucleic acid including the base sequence represented by SEQ ID NO: 2. The base sequence of SEQ ID NO: 2 is: ATGAACAAGAACATCATTTACGGTCCACCAC-CCGTTTATCCTCTTGACGATGGAACAGG TGGC-GAGCAATTGTACAAATGCATTTTAAGGTACGC-CAAAATTCCTGAATGCGTTGCTT TGACAAGCGCGCATACTAAAGAAAGCATTTTATAC-GAAGAATTATTGCAATTAACGTGC AAATTAGCT-CAAAGCCTAAAGCGATGCGGAATTA-CAAGAAATAGTACTATCGCTGTGTG CAGTGAAAACAATCTGCAATACTTTATACCCAT-TATCGCCGGCTTATACATTGGAGCTG CCACAGCA-GCTGTTAATAACAGATACAACGAACGAGAACTTAC-CGATATTTTAAATTTG TCAAAACCGGATATAATTTTTT-GCTCTAAAGAAACATTGCCAAAAATTTGTCAAGT-CAA AAAGAAACTGAATTACATTAAAGAAATTATT-GTTCTCGATAGCAAACACGATAGTGAGT TGGCTCAATGTTAGATAATTTTATTTCCCACAATT-GCAACAAAGATTTCGATGCGTAT CAGTTTAAGC-CAAGCTCTTTTAACCGTAACGAGCAAGTAGGTT-TAATACTAAATTCGTC AGGATCGACAGGTCTTCCGAAAGGTGTAAT-GCTAACGCATAAAAACTTAGTCGTGCGAT TTTCT-CATTGCAAAGATCCCGTTTTTGG-TAACATAATTTCTCCGGGTACTGCCATTTTA ACAGTTATACCGTTTCACCATGGTTTTGGTATGTT-TACAACTTTGGGGTATTTTACATG TGGATTTCGAAT-TGTTTTAATGCACACGTTTTACGAAAAGTTGTTTTT-GCAAGCGCTAG AAGATTATAAAGTTGAAAGTACTTTATTGGTAC-CTACTTTAATGACGTTTTTTGCAAAA AGCGCTT-TAGTAGATAAATACAATTTGCCGTATT-TAAAGGAAATTGCATCGGGTGGTGC CCCGCTATCTAAAGAAATCGGCGAAGCAGTAG-CACGAAGGTTTAAACTAAACGCAATTA GACAAGGTTATGGTTTAACTGAAACTACATCTGCT-GTATTAATTACACCAGAAAGTGAA ACAGTACCTG-GATCCATAGGAAAGGTGGTGCCATTTTTCGCG-GCTAAAATAATTGATCA TCGAACTGGTAAAGCATTAGGACCGAACGAAGT-TGGAGAATTATGTTTTAAAGGGGATA TGATTAT-GAAAGGTTACTGTAATAATATTGAAGCAACTAAT-GCTATAATCGACAACGAC GGGTGGCTCCATTCGGGCGATCTTGGGTATTA-CAACGACGATAAACATTTTTTCATAGT AGATC-GACTTAAGTCTATAATAAAATACAAAGGATAT-CAAGTCGCTCCTGCTGAATTAG AAGGTATATTGTTAACTCATCCAAGTATTATG-GACGCTGGTGTAACTGGTATACCCGAT GACAACGCCGGAGAACTACCAGCAGCATGTGTT-GTGGTTAAACCAGGACGGCATCTTAC AGAAGAAATGTCATAAATTACGTATCGAGT-CAAGTGTCATCCGTAAAGAGATTACGCG GCGGT-GTGCGCTTCCTCGATGAAATTCCCAAAGGATC-CACAGGAAAAATCGATACTACA GCTTTGAAACAAATTCTGCAAAAACCGAACTG-CAAATTATAA. The gene having this sequence is cloned from Luciola sp2 and encodes SP2 luciferase.

The nucleic acid of an embodiment may be those containing base sequence of the wild-type luciferase gene and those including base sequence of the mutant luciferase gene having a mutation therein. Here, the mutant luciferase gene may be a gene in which specific bases in the base sequence, for example, several bases are substituted, deleted, and/or added, as long as it can exhibit the characteristics, that is, higher luminous intensity in comparison to conventional luciferases. Mutation of base sequence includes those which do not cause alteration of the amino acid sequence to be encoded. Namely, the nucleic acid of an embodiment includes those containing a mutated luciferase gene which encodes wild-type luciferase.

An example of mutation which does not cause alternation of the amino acid sequence to be encoded is mutation which cancels recognition sequence of a specific restriction enzyme. Because of this mutation, the nucleic acid including the gene is not digested by the restriction enzyme, but the gene can encode the protein having the same amino acid sequence as that of before mutation. Such mutation can be achieved by conversion of the codons constituting the recognition sequence of the restriction enzyme to the synonymous codons. Such mutation is useful when the recognition sequence of the restriction enzyme to be used for genetic recombination is in the gene. In this case, fragmentation of the nucleic acid can be prevented by canceling the recognition sequence of the gene in advance, thereby facilitating genetic recombination. An example of such a base sequence is that represented by SEQ ID NO: 3. In the sequence, the recognition sequences of BamHI and EcoRI are cancelled.

Another example of mutation which does not cause alteration of an amino acid to be coded is mutation which optimizes codons of a gene for expression in a specific organism species. Here, the term "optimization" means to substitute codons of a gene contained in a nucleic acid with codons which has high codon frequency in a specific organism species. If the optimization is carried out, expression of a gene in a specific organism species is enhanced in comparison to a case where optimization is not carried out. The luciferase gene of an embodiment is derived from fireflies, and thus it is considered that the farther the organism species to which the gene is introduced is from a firefly in terms of taxonomy, the higher effects can be obtained by optimization. In the present invention, a specific organism species is, for example, a bacterial cell, yeast cell, and mammal cell. A mammal cell is, for example, a mouse cell, monkey cell, and human cell.

An example of the nucleic acid of an embodiment including the base sequence in which codons are optimized and which encodes luciferase, is a nucleic acid including the base sequence represented by SEQ ID NO: 4. The base sequence of SEQ ID NO: 4 is: ATGAACAAGAACAT-CATCTACGGCCCTCCCCCCGTGTACCCCCTGGAT-GATGGCACAGG CGGCGAGCAGCTGTACAAGTG-CATCCTGAGATACGCCAAGATCCCCGAGTGCGTG-GCCC TGACCAGCGCCCACACCAAAGAGAGCATC-CTGTACGAGGAACTGCTGCAGCTGACCTGC AAGCTGGCCCAGAGCCTGAAGAGATGCGGCAT-CACCCGGAACAGCACAATCGCCGTGTG CAGCGA-GAACAACCTGCAGTACTTCATCCCCATCATTGCCG-GCCTGTACATCGGAGCCG CCACAGCCGCCGTGAACAACCGGTACAACGAGA-GAGAGCTGACCGACATCCTGAACCTG AGCAAGC-CCGACATCATCTTTTGCTCCAAAGAGACACTGC-CCAAGATCTGCCAGGTCAA GAAGAAGCTGAACTACATCAAAGAAATCATCGT-GCTGGACAGCAAGCACGACAGCGAGC TGGCTCA-GTGTCTGGACAACTTCATCAGCCACAACTG-CAACAAGGACTTCGACGCCTAC CAGTTCAAGCCCAGCAGCTTCAACCGGAAC-GAACAGGTCGGCCTGATCCTGAACAGCAG CGGGCA-GCACCGGCCTGCCCAAGGGCGTGATGCTGACCCA-CAAGAACCTGGTGGTGCGCT TCAGCCACTGCAAGGACCCCGTGTTCGGCAACAT-CATCAGCCCCGGCACCGCCATCCTG ACCGTGATC- CCTTTCCACCACGGCTTCGGCATGTTCACCAC-
CCTGGGCTACTTCACCTG
TGGCTTCCGGATCGTGCTGATGCACACCTTCTAC-
GAGAAGCTGTTCCTGCAGGCCCTGG AAGATTA-
CAAGGTGGAAAGCACCCTGCTGGTGCCTACCCT-
GATGACCTTCTTCGCCAAG
AGCGCCCTGGTGGACAAGTACAACCTGCCCTACCT-
GAAAGAGATCGCCAGCGGCGGAGC CCCCCTGAG-
CAAAGAAATCGGCGAGGCCGTGGCCAGACGGT-
TCAAGCTGAACGCCATCC
GGCAGGGCTACGGCCTGACCGAGACAACCAGCGC-
CGTGCTGATCACCCCCGAGAGCGAG ACAGTGC-
CCGGCAGCATCGGCAAGGTGGTGCCATTCTTCGC-
CGCCAAGATCATCGACCA
CCGGACCGGCAAGGCCCTGGGCCCTAAT-
GAAGTGGGCGAGCTGTGCTTCAAGGGCGACA
TGATCATGAAGGGCTACTGCAACAACATCGAGGC-
CACCAACGCCATCATCGACAACGAC GGCTGGCTG-
CACAGCGGCGATCTGGGCTACTACAACGACGA-
CAAGCACTTCTTCATCGT
GGACCGGCTGAAGTCCATCATCAAGTACAAGGGC-
TACCAGGTGGCCCCTGCCGAGCTGG AAGGCATC-
CTGCTGACACACCCCAGCATCATGGATGCCGGCGT-
GACCGGCATCCCCGAC
GATAATGCCGGCGAGCTGCCTGCCGCCTGCGTG-
GTGGTGAAACCCGGCAGACACCTGAC CGAG-
GAAAACGTGATCAACTACGTGTCCAGCCAGGT-
GTCCAGCGTGAAGCGGCTGAGAG
GCGGCGTGCGGTTCCTGGACGAGATC-
CCTAAGGGCTCCACCGGCAAGATCGACACCACC
GCCCTGAAGCAGATCCTGCAGAAGCCCAACTG-
CAAGCTGTGA. In the nucleic acid, the recognition sequences of BamHI and EcoRI are cancelled and codons are optimized for expression in a mammal cell.

The nucleic acid of an embodiment contains those including luciferase gene provided with Kozak sequence. Kozak sequence is sequence comprised of initiation codon and plural base sequences located in before and after the initiation codon. It has been proved that expression amount of the gene is increased because of presence of Kozak sequence. With respect to Kozak sequence, common sequence has been found in each organism species or biome. The nucleic acid including Kozak sequence of an embodiment has Kozak sequence corresponding to the organism species to which it is introduced. For example, in the case where it is introduced into a mammal cell, the nucleic acid includes sequence gccrccatgg (SEQ ID NO: 5) as Kozak sequence, in which r means guanine or adenine. A luciferase gene provided with Kozak sequence may be a wild-type gene and mutant gene in which codons are optimized in the above-mentioned manner. An example of the nucleic acid of the embodiment including luciferase gene sequence provided with Kozak sequence is a nucleic acid including base sequence represented by SEQ ID NO: 31. In these nucleic acids, the recognition sequences of BamHI and EcoRI are cancelled, codons are optimized corresponding to a mammal cell, and Kozak sequence corresponding to a mammal cell is provided.

The present invention includes a vector having these nucleic acids. The vector may contain a nucleic acid and the like containing sequence for regulating expression or sequence of a marker gene other than the nucleic acid encoding luciferase.

The present invention includes a luminescence probe. The luminescence probe may contain wild-type luciferase or the mutants thereof. Preferably, the probe is modified by conventional techniques to improve the utilization of the probe. Further, the luminescence probe of an embodiment may be applied for various purposes (imaging, photometry, luminometer and the like) with regard to various in vivo samples or in vitro samples.

The present invention relates to a method for analyzing function in a cell by utilizing the luciferase of an embodiment. The method comprises introducing the luciferase of an embodiment into a cell and detecting luminescence of the luciferase with an imaging apparatus. For example, the luciferase gene of the embodiment is introduced in downstream of a specific expression regulation region in DNA, and the expression of luciferase is detected based on the presence or absence of luminescence, thereby achieving the determination of the function of the expression regulation region.

The present invention relates to a method for analyzing an intracellular protein utilizing the luciferase of an embodiment. The method comprises introducing a fusion protein comprised of luciferase of an embodiment and a protein to be analyzed and; and detecting luminescence of the luciferase with an imaging apparatus.

The method contains observation of localization of the protein to be analyzed in a cell and time-course observation (time-lapse) of the localization. The method contains not only the protein localization but also mere confirmation whether the protein is expressed or not. Cells to be used are nonexclusive, and may be those which can be ordinarily used in a field of cell imaging. Further, the proteins to be analyzed are also nonexclusive, and they can be selected in accordance with the aim of research. The protein may be those which essentially exist in a cell to be used, or may be heterogeneous or modified proteins which are do not essentially exist in a cell.

Upon introducing a fusion protein into a cell, known methods for introducing can be applied. One of them is a method for directly introducing a fusion protein purified in vitro into a cell. For example, a fusion protein can be directly injected into a cell by a microinjection method. Or, a cell is incubated in culture medium containing a fusion protein, thereby introducing the fusion protein into a cell by endocytosis. Another method is to introduce a nucleic acid containing the base sequence encoding the fusion protein, followed by expression of the fusion protein in a cell. For example, an expression vector containing the nucleic acid is introduced into a cell by a calcium phosphate method, lipofection, electroporation, and the like, thereby achieving expression of the fusion protein from the expression vector. Here, the gene of a fusion protein is those containing the luciferase gene of an embodiment and the gene of the protein to be analyzed, in which the luciferase gene and the gene of the protein are linked so that each of them can be normally translated.

Upon detection of luminescence of luciferase with an imaging apparatus, well known detection methods can be applied. For example, luciferase luminescent reaction is caused by adding luciferin, ATP, $Mg^{2+}$ ions, and the like are added to a cell expressing a fusion protein containing lucifarese as appropriate, and the luminescence caused can be detected by an imaging apparatus. The imaging apparatus is a microscope provided with a filter for capturing luminescence. The localization of a protein can be specified by using a microscope based on the information obtained through identification of position of luminescence in a cell. As an imaging apparatus, a microscope provided with function which enables time-course image pickup can be used, and time-course observation can be achieved by the microscope.

Example 1

Cloning of Luciferase Gene

1. Materials

Firefly larvae collected in the state of Perak, Malaysia were used as materials. The used firefly has been proved to belong to genus *Luciola*, but a scientific name has not been assigned thereto. In this disclosure, the species is referred to as *Luciola* sp2 or sp2.

2. Extraction of Total RNA and Synthesis of cDNA

A luminescent organ was cut off from firefly larvae. To Lysing Matrix D tube (MP-Biomedicals, LLP), which is a tube containing beads for homogenizing tissues and cells, added were the collected luminescent organ and 1 mL of total RNA extraction reagent TRIzol Reagent (Invitrogen). The tube was installed in a homogenization system FastPrep 24 (MP-Biomedicals, LLP) or FastPrep FP100A (MP-Biomedicals Co., Ltd.), and the firefly luminescent organ was homogenized in the reagent at speed of 6.5 m/s and time of 45 seconds. Upon completion thereof, the tube was taken out from the system and placed on ice for 30 minutes. Consequently, the homogenizing process was repeated once under the same condition.

In the next step, according to the instructions of total RNA extraction reagent TRIzol Reagent, total RNA was isolated and purified from the homogenized solution. 100 µl of the obtained mRNA solution was precipitated and concentrated by an ethanol precipitation method. From a full length cDNA was synthesized from the precipitated and concentrated total RNA with use of a full length cDNA synthesis reagent GeneRacer (Invitrogen) according to the manual. 20 µl of the obtained cDNA solution was subjected to the genetic experiments described below as a firefly full length cDNA library.

3. Identification of 5' Terminal Side of Firefly Luciferase Gene 3-1. Preparation of Primers to be Used for Rapid Amplification of cDNA End (RACE) Method Cloning of a novel luciferase gene was performed by a polymerase chain reaction (PCR) method. The primers used for the PCR were prepared as described below based on the amino acid sequence of luciferase from a known closely-related species.

In order to confirm the amino acid region which is highly conserved in firefly luciferases, amino acid sequences of 10 types of firefly luciferase which have been already published are compared to one another with use of sequence information analysis software DNASIS Pro (Hitachi Software Engineering Co., Ltd.). The closely-related species used for the comparison is *Lampyris noctiluca* (Registration No. CAA61668), *Luciola cruciata* (Registration No. P13129), *Luciola lateralis* (Registration No. Q00158), *Luciola mingrelica* (Registration No. Q26304), *Hotaria parvula* (Registration No. AAC37253), *Photinus pyralis* (Registration No. BAF48390), *Photuris pennsylvanica* (Registration No. Q27757), *Pyrocoelia miyako* (Registration No. AAC37254), *Pyrocoelia rufa* (Registration No. AAG45439), and *Rhagophthalmus ohbai* (Registration No. BAF34360).

Consequently, it was proved that amino acid sequence L-I-K-Y-K-G-Y-Q-V (SEQ ID NO: 6) located in the proximity of 440th residue on C terminal side of firefly luciferase is highly conserved. Based on the codons encoding these 9 amino acids, the base sequence was predicted, and 12 types of firefly luciferase specific mixed primers were designed to be applied to 5' terminal RACE PCR. The names and sequences of these primers are: flexLuc5-ATA (5'-ACY TGR TAN CCY TTA TAT TTA AT-3': SEQ ID NO: 7), flexLuc5-ATG (5'-ACY TGR TAN CCY TTA TAT TTG AT-3': SEQ ID NO: 8), flexLuc5-ATT (5'-ACY TGR TAN CCY TTA TAT TTT AT-3': SEQ ID NO: 9), flexLuc5-ACA (5'-ACY TGR TAN CCY TTA TAC TTA AT-3': SEQ ID NO: 10), flexLuc5-ACG (5'-ACY TGR TAN CCY TTA TAC TTG AT-3': SEQ ID NO: 11), flexLuc5-ACT (5'-ACY TGR TAN CCY TTA TAC TTT AT-3': SEQ ID NO: 12), flexLuc5-GTA (5'-ACY TGR TAN CCY TTG TAT TTA AT-3': SEQ ID NO: 13), flexLuc5-GTG (5'-ACY TGR TAN CCY TTG TAT TTG AT-3': SEQ ID NO: 14), flexLuc5-GTT (5'-ACY TGR TAN CCY TTG TAT TTT AT-3': SEQ ID NO: 15), flexLuc5-GCA (5'-ACY TGR TAN CCY TTG TAC TTA AT-3': SEQ ID NO: 16), flexLuc5-GCG (5'-ACY TGR TAN CCY TTG TAC TTG AT-3': SEQ ID NO: 17), flexLuc5-GCT (5'-ACY TGR TAN CCY TTG TAC TTT AT-3': SEQ ID NO: 18); Y, R, and N in the primer sequences indicating mixed bases. The synthesis of these primers was commissioned to Life Technologies, Japan, Co., Ltd.

3-2. Cloning of 5' Terminal Side of Firefly Luciferase Gene by 5'-RACE PCR

With use of the firefly full-length cDNA library which was prepared in such a manner described above as a template, 5'-RACE RCP was performed using 12 types of specific mixed primers prepared in such a manner described above; GeneRacer5'Primer (5'-CGA CTG GAG CAC GAG GAC ACT GA-3': SEQ ID NO: 19) and GeneRacer5'Nested Primer (5'-GGA CAC TGA CAT GGA CTG AAG GAG TA-3': SEQ ID NO: 20). GeneRacer5' Primer and GeneRacer5' Nested Primer were those contained in a full length cDNA synthesis reagent GeneRacer kit (Invitrogen). In order to amplify the luciferase gene efficiently by 5'-RACE PCR, with use of the gene amplified once by PCR as a template, nested PCR which amplifies the gene further specifically with an inside primer pair was performed. The PCR was carried out with use of polymerase Ex-Taq (Takara Bio Inc.) according to the manual.

As the first PCR, the luciferase gene was amplified with use of 12 types of primer pairs composed of any one of the aforementioned 12 types of specific mixed primer and GeneRacer5' Primer. To 10 µl of PCR reaction solution comprising 10×Ex Tag Buffer diluted tenfold (20 mM $Mg^{2+}$ plus), dNTP Mixture at a final concentration of 0.2 mM (2.5 mL for each base), TaKaRa Ex Taq (5 U/µl) at a final concentration of 0.05 U/µl, one of 12 types of primers at a final concentration of 1.0 µM, and GeneRacer3' Primer at a final concentration of 0.3 µM, added was 0.2 µl of firefly full-length cDNA library solution. Here, the concentration of the firefly full-length cDNA library solution was not determined. In the PCR reaction, the solution was thermally denatured for 2 minutes at 94° C., and then the cycle consisting of 30 seconds at 94° C., 30 seconds at 45° C., and 90 seconds at 72° C. was repeated 30 times, followed by an elongation reaction at 72° C. for 5 minutes. After the PCR reaction, 1 µl of the PCR reaction solution was applied to 1% tris acetic acid buffer (TAE) agarose gel electrophoresis, and observed bands of amplified genes under exposure of ultraviolet after dyeing with ethidium bromide. In all of the 12 reaction solution, a slight gene amplification was confirmed, and thus a nested PCR reaction was carried out with use of each PCR reaction solution as a template, in such a manner described below.

As nested PCR, amplification of luciferase gene was carried out with use of four kinds of primer pairs each consisting of one of four types out of 12 types of primers used in the first PCR and GeneRacer3' Nested Primer. To 10 µl of PCR reaction solution comprising 10×Ex Tag Buffer (20 mM Mg$^{2+}$ plus) diluted tenfold, dNTP Mixture at a final concentration of 0.2 mM (2.5 mL for each base), TaKaRa Ex Taq (5 U/μl) at a final concentration of 0.05 U/μl, one of 12 types of primers at a final concentration of 1.0 μM, and GeneRacer3' Primer at a final concentration of 0.3 μM, added was 10 μl of the first PCR reaction solution diluted ten fold with sterilized water as a template. In the PCR reaction, the solution was thermally denatured for 2 minutes at 94° C., and then the cycle consisting of 30 seconds at 94° C., 30 seconds at 45° C., and 90 seconds at 72° C. was repeated 30 times, followed by an elongation reaction at 72° C. for 5 minutes. After the PCR reaction, 1 μl of PCR reaction solution was applied to 1% tris acetic acid buffer (TAE) agarose gel electrophoresis, and observed bands of amplified genes under exposure of ultraviolet after dyeing with ethidium bromide. The combination condition of primers which efficiently amplified the gene in the proximity of about 1.4 kbp was confirmed.

3-3. Determination of Base Sequence of Gene Amplified by 5'-RACE

In order to determine the base sequence of the gene amplified by 5'-RACE, purification by gel extraction, subcloning, and direct sequencing were carried out. The details are given below.

The PCR was carried out with use of the combination which efficiently amplified the gene in proximity of 1.4 kbp was performed (final volume 20 μl), and then the objective gene fragments were collected with use of gel extraction. Gel extraction was carried out with use of Wizard SV Gel and PCR Clean-UP System (Promega KK) according to the manual thereof. Subcloning of the PCR products extracted from gel were carried out by means of TA cloning. TA cloning was carried out with use of pGEM-T Easy Vector System (Promega KK) according to the manual thereof. Subsequently, the vector DNA was transformed to *Escherichia coli* (TOP10 strain or DH5α strain), and insert-positive colonies were selected by means of blue-white screening. The selected colonies were subjected to a direct colony PCR, and confirmed that the objective gene was inserted. In a direct colony PCR, a primer pair consisting of M13-F(-29) Primer (5'-CAC GAC GTT GTA AAA CGA C-3': SEQ ID NO: 21) and M13 Reverse (5'-GGA TAA CAA TTT CAC AGG-3': SEQ ID NO: 22) was used. To 10 μl of PCR reaction solution comprising 10×Ex Taq Buffer (20 mM Mg$^{2+}$ plus) diluted tenfold, dNTP Mixture at a final concentration of 0.2 mM (2.5 mL for each base), TaKaRa Ex Taq (5 U/μl) at a final concentration of 0.05 U/μl, and a primer pair at a final concentration of 0.2 μM, added was a small amount of colony of *Escherichia coli*. In the PCR reaction, the solution was thermally denatured for 1 minute at 94° C., and then the cycle consisting of 30 seconds at 94° C., 30 seconds at 50° C., and 2 minutes at 72° C. was repeated 25 times, followed by an elongation reaction at 72° C. for 2 minutes. After the PCR reaction, 2 μl of PCR reaction solution was applied to 1% TAE agarose gel electrophoresis, and observed bands of amplified genes under exposure of ultraviolet after dyeing with ethidium bromide.

With regard to the PCR reaction solution for which amplification was confirmed, the base sequence of the gene was determined by means of a direct sequencing method. With use of PCR product purification kit ExoSAP-IT (GE Healthcare Bioscience), the extra dNTP and primers contained in the PCR reaction solution was removed, and a template for the PCR direct sequencing was prepared. With use of BigDye Terminator v3.1 Cycle Sequencing Kit (Applied Biosystems), a sequencing reaction solution containing the template was prepared, and a sequencing reaction was performed by a thermal cycler. Purification and sequencing of the PCR products were each carried according to the manuals thereof. After the sequencing reaction, the reaction products were purified as described below. 2.5 times of weight of 100% ethanol was added to the reaction solution, and then a nucleic acid was precipitated by a centrifuge. After the supernatant was removed, the precipitate was dried. To the purified precipitate, 15 of Hi-Di Formanmide (Applied Biosystems) was added and dissolved. The solution was subjected to thermal denaturation at 94° C. for 2 minutes, and further rapidly cooled on ice, thereby providing a sample for determination of base sequence. With respect to the sample, the base sequence was determined by using Applied Biosystems 3130×1 genetic analyzer (Applied Biosystems). The analytical method was carried out according to the manual.

The obtained gene sequence was analyzed by the "sequence linking" function of sequence information analysis software DNASIS Pro. With respect to the sequence, homology research was performed by using blastx search provided by the National Center for Biotechnology Information (NCBI), and it was confirmed that the sequence indicates a high homology with base sequences of known firefly luciferases. The base sequence obtained by the aforementioned experiments and analyses was determined as being located on 5' terminal side of a novel firefly luciferase gene. The obtained base sequence is shown in SEQ ID NO: 23 as base sequence in a nontranslated region on 5'-terminal side of a *Luciola* sp2 firefly luciferase gene.

4. 3' Race RCR of Firefly Luciferase Gene and Acquisition of Full-Length cDNA 4-1. Design of Primers to be Used for 3' Race PCR Based on the sequence in the nontranslated region on 5' terminal side of luciferase gene obtained by the 5' Race PCR experiment, primers to be used for 3' RACE and those used for Nested PCR were prepared. Synthesis of primers was commissioned to Life Technologies, Japan.

4-2. 3'Race PCR for Acquisition of Full-Length Firefly Luciferase

With use of the firefly full-length cDNA library prepared as described above as a template, 3'-Race PCR was performed by applying the primer prepared from the base sequence of the nontranslated region on 5' terminal side of objective firefly luciferase (AACTCTATCAT-GAACAAGAACATCATTTAC, SEQ ID NO: 24), GeneRacer3' Primer (5'-GCT GTC AAC GAT ACG CTA CGT AAC G-3'; SEQ ID NO: 26), and Gene Racer3' Nested Primer (5'-CGC TAC GTA ACG GCA TGA CAG TG-3': SEQ ID NO: 27). The used GeneRacer3' Primer and GeneRacer3' Nested Primer were contained in a full-length cDNA synthesis reagent GeneRacer kit (Invitrogen). In order to efficiently amplify luciferase gene by 3'-RACE PCR, the genes once amplified by PCR were used as a template, and the nested PCR which further specifically amplifies the gene was carried out with use of the inside primer pair. The PCR was carried out with use of polymerase Ex-Taq (Takara Bio Inc.) according to the manual.

As the first PCR, a primer pair comprised of a primer prepared from base sequence of the nontranslated region on 5' terminal side and GeneRacer 3' Primer was used to amplify the luciferase gene. To 20 μl of PCR reaction comprising 10×Ex Taq Buffer (20 mM Mg$^{2+}$ plus) diluted tenfold, dNTP Mixture at a final concentration of 0.2 mM (2.5 mL for each base), TaKaRa Ex Taq (5 U/μl) at a final concentration of 0.05 U/μl, and primers at a final concentration of 0.3 μM, added was 0.4 μl of firefly full-length cDNA library solution. Here, the concentration of the firefly full-length cDNA library solution was not determined. In the PCR reaction, the solution was thermally denatured for 2 minutes at 94° C., and then the cycle consisting of 30 seconds at 94° C., 30 seconds at 50° C., and 2 minutes at 72° C. was repeated 30 times, followed by an elongation reaction at 72° C. for 5 minutes. After the PCR reaction, 1 µl of the PCR reaction solution was applied to 1% tris acetic acid buffer (TAE) agarose gel electrophoresis, and observed bands of amplified genes under exposure of ultraviolet after dyeing with ethidium bromide. Slight gene amplification was confirmed, and thus nested PCR was performed with use of the PCR reaction solution as a template.

As the Nested PCR, the luciferase gene was amplified with use of a primer pair consisting of a primer for Nested PCR (AACTCTATCATGAACAAGAACATCATTTACG-GTCCA, SEQ ID NO: 25) and GeneRacer3' Nested Primer (5'-CGC TAC GTA ACG GCA TGA CAG TG-3', SEQ ID NO: 27). To 10 µl of PCR reaction solution comprising 10×Ex Taq Buffer (20 mM $Mg^{2+}$ plus) diluted tenfold, dNTP Mixture at a final concentration of 0.2 mM (2.5 mL for each base), TaKaRa Ex Taq (5 U/µl) at a final concentration of 0.05 U/µl, and primers at a final concentration of 0.3 µM, added was 1.0 µl of a solution prepared by diluting the first PCR reaction solution in tenfold with sterilized water, as a template. In the PCR reaction, the solution was thermally denatured for 2 minutes at 94° C., and then the cycle consisting of 30 seconds at 94° C., 30 seconds at 50° C., and 2 minutes at 72° C. was repeated 30 times, followed by an elongation reaction at 72° C. for 5 minutes. After the PCR reaction, 1 µl of PCR reaction solution was applied to 1% tris acetic acid buffer (TAE) agarose gel electrophoresis, and observed bands of amplified genes under exposure of ultraviolet after dyeing with ethidium bromide. It was confirmed that the gene was efficiently amplified at about 2 kbp.

4-3. Determination of Base Sequence of the Gene Amplified by 3'-Race

In order to identify the base sequence amplified by 3'-RACE, PCR product was purified by gel extraction, followed by subcloning and direct sequencing. The details are given below.

With the combination of primers which efficiently amplified the genes at about 2 kbp, PCR (final volume 20 µl) was carried out, and the objective gene fragments were collected by means of gel extraction. The gel extraction was carried out with use of Wizard SV Gel and PCR Clean-Up System (Promega KK) according to the manual. The subcloning of the PCR product extracted from gel was carried out by means of TA cloninig. The TA cloning was performed with us of pGEM-T Easy Vector System (Promega KK) according to the manual. Subsequently, the vector DNA was transformed to E. Coli (TOP10 strain or DH5α strain), and the insert positive colonies were selected by means of blue-white screening. The selected colonies were subjected to a direct colony PCR, and confirmed that the gene was introduced. In the direct colony PCR, a primer pair consisting of M13-F(-29) Primer (5'-CAC GAC GTT GTA AAA CGA C-3': SEQ ID NO: 21) and M13 Reverse (5'-GGA TAA CAA TTT CAC AGG-3': SEQ ID NO 22) was used. To 10 µl of PCR reaction comprising 10×Ex Taq Buffer (20 mM $Mg^{2+}$ plus) diluted tenfold, dNTP Mixture at a final concentration of 0.2 mM (2.5 mL for each base), TaKaRa Ex Taq (5 U/µl) at a final concentration of 0.05 U/µl, and primers at a final concentration of 0.2 µM, added was a small amount of E. coli colony as a template. In the PCR reaction, the solution was thermally denatured for 1 minute at 94° C., and then the cycle consisting of 30 seconds at 94° C., 30 seconds at 50° C., and 2 minutes at 72° C. was repeated 25 times, followed by an elongation reaction at 72° C. for 2 minutes. After the PCR reaction, 2 µl of the PCR reaction solution was applied to 1% tris acetic acid buffer (TAE) agarose gel electrophoresis, and observed bands of amplified genes under exposure of ultraviolet after dyeing with ethidium bromide.

As for the PCR reaction solutions for which the amplification was confirmed, the base sequence of the gene was determined by a direct sequencing method. With use of a PCR product purification kit ExoSAP-IT (GE Healthcare Bioscience), extra dNTP and primers containing the PCR reaction solution were removed, and prepared a template for PCR direct sequencing. A sequencing reaction solution was prepared with use of BigDye Terminator v3.1 Cycle Sequencing Kit (Applied biosystems), and the sequencing reaction was carried out by a thermal cycler. The primers used for sequencing were a vector primer or a primer specific to a gene. Purification of the PCR products and sequencing were each performed according to the manual. After the sequencing reaction, the purification was performed as follows. To the reaction solution, added was 2.5 times by weight of 100% ethanol, followed by precipitation of the nucleic acid with a centrifuge. After removing the supernatant, the precipitate was washed by adding 70% ethanol and the nucleic acid were precipitated by a centrifuge. After removing the supernatant, the precipitate was dried finally. To the purified precipitate, 15 µl of Hi-Di Formamide (Applied Biosystems) was added and dissolved. The solution was thermally denatured at 94° C. for 2 minutes, cooled on ice, and used as a sample for determination of base sequence. With respect to the sample, the base sequence was determined with use of Applied Biosystems 3130×1 genetic analyzer (Applied Biosystems). The analytical method of the base sequence was carried out according to the manual.

A full-length firefly luciferase gene was obtained by sequencing. As for the base sequence (SEQ ID NO: 2) or the sequence translated into the amino acid (SEQ ID NO: 1), the homology search was performed by utilizing the blastx or blastp search provided by NCBI. In each search, it was confirmed that the base sequence has high homology with the base sequences of known firefly luciferases. The base sequence obtained in the experiments and analysis described above was determined as a full-length cDNA sequence of a novel firefly luciferase.

Hereinafter, the novel luciferase is referred to as SP2 luciferase.

Example 2

Determination of Enzymatic Parameters of Novel Luciferase

1. Protein Expression of Novel Firefly Luciferase Gene

For expressing firefly luciferase gene in E. coli, it was introduced into a pRSET-B vector (Invitrogen). According to the standard method, the gene expression vector was constructed by experiments described below.

1-1. Modification of Recognition Site of Restriction Enzyme of Novel Firefly Luciferase Gene According to the base sequence determined as described above, the novel luciferase gene contains the recognition sequence of restriction enzymes BamHI and EcoRI. The genetic modification was carried out so that the amino acid sequence of luciferase was maintained and the recognition sequences in these base sequences were removed. This treatment was carried out for the purpose of facilitating the introduction of luciferase gene into an expression vector which is explained below. The introduction of genetic mutation was carried out by following the method described in "a experimental method of gene functional inhibition—from simple and secure gene function analysis to application to gene therapy" edited by Kazunari Taira, Yodosha, published in 2001, pages 17-25). The base sequence after mutation introduction is represented by SEQ ID NO: 3.

1-2. Introduction of Novel Firefly Luciferase into Expression Vector

In order to introduce luciferase gene to a region between BamHI site and EcoRI site of pRSET-B vector, a primer comprising intiation codon and recognition sequence of restriction enzyme BamHI GGATCC therebefore, and a primer comprising termination codon and recognition sequence of restriction enzyme EcoRI GAATTC thereafter were prepared. With use of the primer pair, a fragment including the aforementioned restriction enzyme recognition sites on both terminals of luciferase gene was amplified. The PCR was carried out with use of polymerase KOD-Plus (Toyobo Co., Ltd.) according to the manual.

To 10 µl of PCR reaction comprising 10×PCR Buffer diluted ten fold, dNTP Mixture at a final concentration of 0.2 mM (2.5 mL for each base), $MgSO_4$ at a final concentration of 1.0 mM, Toyobo KOD-Plus (1 U/µl) at a final concentration of 0.02 U/µl, and a primer pair at a final concentration of 0.3 µM, added was 0.4 µl of luciferase gene not including BamHI and EcoRI recognition sequences as a template. In the PCR reaction, the solution was thermally denatured for 2 minutes at 94° C., and then the cycle consisting of 30 seconds at 94° C., 30 seconds at 55° C., and 2 minutes at 68° C. was repeated 30 times, followed by elongation reaction at 68° C. for 5 minutes. After the PCR reaction, 1 µl of PCR reaction solution was applied to 1% tris acetic acid buffer (TAB) agarose gel electrophoresis, and observed bands of amplified genes under exposure of ultraviolet after dyeing with ethidium bromide. The gene amplification was confirmed, and thus this PCR reaction solution was precipitated and concentrated by an ethanol precipitation method, dissolved by adding 4 µl of 10×H Buffer for restriction enzyme treatment, restriction enzymes BamHI (Toyobo Co., Ltd.) and EcoRI (Toyobo Co., Ltd.) of 2 µl each, and 32 µl of sterile deionized ion water, and treated with the restriction enzymes after maintaining the temperature at 37° C. for 2 hours. Subsequently, the reaction solution was precipitated and concentrated by an ethanol precipitation method, and dissolved in sterile deionized ion water. The solution was applied to 1% TAE agarose gel electrophoresis, followed by dyeing with ethidium bromide. The gel containing DNA bands which were confirmed under exposure of ultraviolet were clipped out with a knife. From the clipped gel, DNA was extracted with use of Wizard(R) SV Gel and PCR Clean-UP System (Promega KK). These operations were performed according to the manual. Subsequently, with use of Ligation Pack (Nippon Gene) in accordance with the manual, the extracted DNA was introduced into pRSET-B vector which was treated by BamHI and EcoRI in advance by a similar method. This vector DNA was transformed to E. coli JM109 (DE3) strain and allowed colony formation.

Direct colony PCR was carried out using the obtained colony as a template, and the luciferase gene introduced into pRSET-B was amplified. The direct colony PCR was performed with use of a primer pair of T7 promoter Primer (5'-TAA TAC GAC TCA CTA TAG GG-3': SEQ ID NO: 28) and T7 Reverse Primer (5'-CTA GTT ATT GCT CAG CGG TGG-3': SEQ ID NO: 29). To 10 µl of PCR reaction comprising 10×Ex Taq Buffer (20 mM $Mg^{2+}$ plus) diluted tenfold, dNTP Mixture at a final concentration of 0.2 mM (2.5 mL for each base), TaKaRa Ex Taq (5 U/µl) at a final concentration of 0.05 U/µl, and primers at a final concentration of 0.2 µM, added was a small amount of E. coli colony as a template. In the PCR reaction, the solution was thermally denatured for 2 minutes at 94° C., and then the cycle consisting of 30 seconds at 94° C., 30 seconds at 50° C., and 2 minutes at 72° C. was repeated 25 times, followed by an elongation reaction at 72° C. for 5 minutes. After the PCR reaction, 1 µl of PCR reaction solution was applied to 1% tris acetic acid buffer (TAE) agarose gel electrophoresis, and observed bands of amplified genes under exposure of ultraviolet after dyeing with ethidium bromide.

As for the PCR reaction solution for which amplification was confirmed, the base sequence of the gene was determined by a direct sequencing method. With use of PCR product purification kit ExoSAP-IT, the extra dNTP and primers were removed thereby preparing a template for PCR direct sequencing. The sequencing reaction solution containing the template was prepared by using BigDye Terminator v3.1 Cycle Sequencing Kit, and sequencing reaction was carried out with use of a thermal cycler. A vector primer or a primer specific to the gene was used for sequencing. Purification and sequencing were carried out according to the manual. After sequencing reaction, the reaction product was purified as explained below. 2.5 times by weight of 100% ethanol was added to the reaction solution, and the nucleic acid was precipitated by a centrifuge. After removing the supernatant, the precipitate was washed by adding 70% ethanol and the nucleic acid was precipitated by a centrifuge. After removing the supernatant, the precipitation was finally dried. The purified precipitate was dissolved by adding 15 µl of Hi-Di Formamide (Applied Biosystems). The solution was thermally denatured for 2 minutes at 94° C., cooled on ice, and used as a sample for determination of the base sequence. With respect to the sample, the base sequence was determined by Applied Biosystems 3130×1 Genetic Analyzer, and confirmed that the gene was introduced into a gene expression vector pRSET-B.

2. Purification of a Luminescent Protein 0.5 µl of luciferase vector was added to 50 µl of the E. coli solution containing JM109 (DE3), and the solution was incubated on ice for 10 minutes, then at 42° C. for 1 minute, and incubated on ice for 2 minutes. Subsequently, 50 µl of the E. coli solution was added to 200 µl of SOC culture medium, and incubated during shaking for 20 minutes at 37° C. 100 µl of the incubated sample was streaked to LB culture medium plate (containing 100 µg/ml of Ampicillin) and incubated at 37° C. overnight. On the next day, the obtained colony was incubated in LB culture medium of 500 ml scale at 37° C. for 24 hours and at 18° C. for 24 hours. After the incubation of 48 hours, the fungus body was collected by a centrifuge, resuspended in 0.1 M Tris-HCl solution (pH 8.0), and subjected to be ultrasonic fragmentation. The fragmented solution of the fungus body was subjected to centrifuge separation (15,000 rpm, 10 minutes), and the supernatant was collected by removing the precipitate. To the column having 2 ml of a bed volume, 500 µl of Ni-Agar suspension solution and 2 ml of 0.1 M Tris-HCl were added to equilibrate the column. The collected supernatant was added to the column, and let it pass through the column. While all the supernatant was passed through the column, the operations were all carried out at 4° C. The column was washed with 2 ml of 25 mM imidazole/0.1 M Tris-HCl solution. To the washed column, 2 ml of 500 mM imidazole/0.1 M Tris-Hcl solution was added to elute luciferase. The eluted sample was filtrated with gel filtration column PD-10

(GE Healthcare) and demineralized. The demineralized sample was subjected to ultrafiltration with Vivaspin6 (Sartorius K.K.), and glycerin was added to the concentrated sample to prepare 50% glycerine solution. The solution was preserved at −20° C.

3. Measurement of Luminescence Spectra

With use of LumiFlSpectroCapture (ATTO) as an apparatus for measurement, to a solution of 0.1 M citric acid/0.1 M $Na_2HPO_4$ buffer (pH 6.0-8.0) containing 1 mM D-luciferin, 2 mM of ATP and 4 mM $MgCl_2$, the purified enzyme was added at a final concentration of 1 to 10 μg/ml, and after 15 seconds of addition of the enzyme luminescence spectra was measured. The measurement results were shown in FIG. 1.

FIG. 1 shows that no maximum luminescent wavelength shift of the obtained luciferase has not been observed upon pH change. The luciferase has maximum luminous wavelength at approximately 557 nm at pH 6.0-8.0.

4. Kinetic Analysis 4-1. Determination of Concentrations of D-Luciferin and ATP

A concentration of D-luciferin in a D-luciferin solution and that of ATP in an ATP solution were determined as described below.

With use of UV-Visible Spectrometer (Hitachi), ultraviolet visible absorption spectra were measured for the D-luciferin solution and ATP solution. Based on the measurement results and ε values indicated below, each concentration was calculated.

D-luciferin: λmax 328 nm, ε 18200, pH 5.0

ATP: λmax 259 nm, ε 15400, pH 7.0

The measurements were carried out ten times for each sample, and the average of absorbency was used for the calculation. The Km value was calculated as is described below by using the D-luciferin solution and ATP solution whose concentrations were determined.

4-2. Measurement of Km for D-Luciferin

Under various concentrations of D-luciferin, the luminous intensity was measured for the obtained luciferase. Based on the measurement results, Km values with respect to D-luciferin were calculated.

Twelve types of D-luciferin of various concentrations were prepared by adding D-luciferin to 0.1 M Tris-HCl (pH 8.0). These solutions contain D-luciferin at final concentrations of 0.625, 1.25, 2.5, 5, 10, 20, 40, 80, 160, 320, 480, and 640 μM. These D-luciferin solutions were each injected into 96-hole microplate at an amount of 50 μl. A solution of 0.1 M Tris-HCl (pH 8.0) containing each of the purified luciferase, 4 mM of ATP, and 8 mM of $MgSO_4$ was connected to the standard pump of the luminometer, and the measurements was carried out at the same time as addition of 50 μl of the solution to the well. A Luminescensor (ATTO) was used for the measurements. Measurements were repeated 3 times for each luciferin concentration.

The peak intensity of the obtained photo count value was plotted with respect to luciferin concentration S, defining the initial rate as V. The plots were subjected to curve fitting of Michaelis Menten type, thereby giving Km values. The curve fitting was performed by a nonlinear least-squares method, and the search of the parameter was performed by a Newton method.

4-3. Measurement of Km Value with Respect to ATP

Under various ATP concentrations, the luminous intensity of the obtained luciferase was measured. Based on the results, Km values with respect to ATP was determined.

Various 12 types of ATP solutions were prepared by adding ATP to 0.1 M Tris-HCl (pH 8.0). These solutions contain ATP at final concentration of 5, 10, 20, 40, 80, 160, 320, 480, 640, 800, 1280, 1600, or 1920 μM. These ATP solutions were each injected into 96-hole in a microplate at a volume of 50 μl. 0.1 M Tris-HCl (pH 8.0) solution containing each purified luciferase, 1 mM D-luciferin, and 8 mM $MgSO_4$ was connected to a standard pump of a luminometer, and the measurement was carried out at the same time as addition of 50 μl of the solution to wells. Measurement was repeated 3 times for each ATP concentration.

The peak intensities of the obtained photon count value were plotted with respect to ATP concentration S, with an initial rate V. The plots were subjected to curve fitting of Michaelis Menten type, thereby giving Km value. The curve fitting was performed by a nonlinear least-squares method, and the search of the parameter was performed by a Newton method.

Km values with respect to D-luciferin and Km values with respect to ATP which were determined as described above were shown in Table 1. Table 1 also indicates Km values for known firefly luciferases, measured in a similar manner. GL3 is a luciferase derived from a known firefly, *P. pylaris* (Promega). Further, ELuc, CBG, and CBR are luciferases derived from known click beetles. These known were commercially available from Toyobo and Promega.

TABLE 1

Comparison of Km value

| | Km | |
|---|---|---|
| | D-luciferin (uM) | ATP (uM) |
| SP2 | 4.25 | 188 |
| GL3 | 15.7 | 71.3 |
| ELuc | 12.7 | 182 |
| CBG | 1.44 | 58.4 |
| CBR | 33.3 | 47.1 |

Further, FIG. 2 indicates these Km values as plots with respect to D-luciferin concentration and ATP concentration. This figure shows that SP2 luciferase has higher Km values with respect to ATP and D-luciferin than those of known luciferase.

Example 3

Measurement of Luminous Intensity

The luminous intensity of SP2 luciferase expressed in a mammal cell (HeLa cell) was compared with that of *P. pylaris*.

The fragment of the nucleic acid having the base sequence of SEQ ID NO: 31 and that of Luc2 luciferase of *P. pyralis* from pGL4(Luc2) vector (Promega co.) were inserted into the pF9A CMV hRluc-neo FlexiR vector (Promega) with multi-cloning sites of SgfI and PmeI. The pF9A vectors were each introduced into HeLa cells by a lipofection method, and D-MEM culture medium was exchanged after 24 hours, and the mutant luciferases were expressed in the cells.

The luminescence intensity of the cells was measured by the luminescensor (ATTO) with 2 mM D-luciferin.

Then, the luminescence intensity of each Hela cell was corrected using the luminescence based on *Renilla* luciferase (hRluc) co-expressed by the SV40 prompter of the pF9A vector (Promega) as an internal standard according to the instruction manual of the Dual-Glo Luciferase Assay System (Promega co.).

Intensities of luminescence of sp2 and *P. pyralus* luciferases are shown in FIG. 3.

From FIG. 3, SP2 luciferase was proved to indicate 2.09 times of luminescent intensity in comparison to that of *P. pyralis*.

FIGS. 4 and 5 show luminescent spectra of sp2 and *P. pyralis* luciferases at various temperatures of 25 and 37° C. As shown in FIG. 4, no maximum wavelength shift has been observed upon temperature change in sp2. This result was in contrast to that of *P. pyralis* shown in FIG. 5.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A luciferase comprising an amino acid sequence comprising SEQ ID NO: 30.

2. The luciferase according to claim 1, which emits luminescence such that a maximum luminous wavelength is 557 nm at pH 8.

3. The luciferase according to claim 1, which emits luminescence such that a maximum luminous wavelength falls within a range of 555 to 560 nm over the entire pH range of 5.5 to 8.0.

* * * * *

SEQUENCE LISTING

```
<160> NUMBER OF SEQ ID NOS: 31

<210> SEQ ID NO 1
<211> LENGTH: 544
<212> TYPE: PRT
<213> ORGANISM: Luciola sp2

<400> SEQUENCE: 1

Met Asn Lys Asn Ile Ile Tyr Gly Pro Pro Val Tyr Pro Leu Asp
1               5                   10                  15

Asp Gly Thr Gly Gly Glu Gln Leu Tyr Lys Cys Ile Leu Arg Tyr Ala
                20                  25                  30

Lys Ile Pro Glu Cys Val Ala Leu Thr Ser Ala His Thr Lys Glu Ser
            35                  40                  45

Ile Leu Tyr Glu Glu Leu Leu Gln Leu Thr Cys Lys Leu Ala Gln Ser
    50                  55                  60

Leu Lys Arg Cys Gly Ile Thr Arg Asn Ser Thr Ile Ala Val Cys Ser
65                  70                  75                  80

Glu Asn Asn Leu Gln Tyr Phe Ile Pro Ile Ile Ala Gly Leu Tyr Ile
                85                  90                  95

Gly Ala Ala Thr Ala Ala Val Asn Asn Arg Tyr Asn Glu Arg Glu Leu
                100                 105                 110

Thr Asp Ile Leu Asn Leu Ser Lys Pro Asp Ile Ile Phe Cys Ser Lys
            115                 120                 125

Glu Thr Leu Pro Lys Ile Cys Gln Val Lys Lys Lys Leu Asn Tyr Ile
    130                 135                 140

Lys Glu Ile Ile Val Leu Asp Ser Lys His Asp Ser Glu Leu Ala Gln
145                 150                 155                 160

Cys Leu Asp Asn Phe Ile Ser His Asn Cys Asn Lys Asp Phe Asp Ala
                165                 170                 175

Tyr Gln Phe Lys Pro Ser Ser Phe Asn Arg Asn Glu Gln Val Gly Leu
                180                 185                 190

Ile Leu Asn Ser Ser Gly Ser Thr Gly Leu Pro Lys Gly Val Met Leu
            195                 200                 205

Thr His Lys Asn Leu Val Val Arg Phe Ser His Cys Lys Asp Pro Val
    210                 215                 220

Phe Gly Asn Ile Ile Ser Pro Gly Thr Ala Ile Leu Thr Val Ile Pro
225                 230                 235                 240

Phe His His Gly Phe Gly Met Phe Thr Thr Leu Gly Tyr Phe Thr Cys
                245                 250                 255

Gly Phe Arg Ile Val Leu Met His Thr Phe Tyr Glu Lys Leu Phe Leu
                260                 265                 270

Gln Ala Leu Glu Asp Tyr Lys Val Glu Ser Thr Leu Leu Val Pro Thr
            275                 280                 285

Leu Met Thr Phe Phe Ala Lys Ser Ala Leu Val Asp Lys Tyr Asn Leu
    290                 295                 300
```

```
Pro Tyr Leu Lys Glu Ile Ala Ser Gly Gly Ala Pro Leu Ser Lys Glu
305                 310                 315                 320

Ile Gly Glu Ala Val Ala Arg Arg Phe Lys Leu Asn Ala Ile Arg Gln
                325                 330                 335

Gly Tyr Gly Leu Thr Glu Thr Thr Ser Ala Val Leu Ile Thr Pro Glu
            340                 345                 350

Ser Glu Thr Val Pro Gly Ser Ile Gly Lys Val Val Pro Phe Phe Ala
        355                 360                 365

Ala Lys Ile Ile Asp His Arg Thr Gly Lys Ala Leu Gly Pro Asn Glu
370                 375                 380

Val Gly Glu Leu Cys Phe Lys Gly Asp Met Ile Met Lys Gly Tyr Cys
385                 390                 395                 400

Asn Asn Ile Glu Ala Thr Asn Ala Ile Ile Asp Asn Asp Gly Trp Leu
                405                 410                 415

His Ser Gly Asp Leu Gly Tyr Tyr Asn Asp Asp Lys His Phe Phe Ile
            420                 425                 430

Val Asp Arg Leu Lys Ser Ile Ile Lys Tyr Lys Gly Tyr Gln Val Ala
        435                 440                 445

Pro Ala Glu Leu Glu Gly Ile Leu Leu Thr His Pro Ser Ile Met Asp
    450                 455                 460

Ala Gly Val Thr Gly Ile Pro Asp Asp Asn Ala Gly Glu Leu Pro Ala
465                 470                 475                 480

Ala Cys Val Val Val Lys Pro Gly Arg His Leu Thr Glu Glu Asn Val
                485                 490                 495

Ile Asn Tyr Val Ser Ser Gln Val Ser Val Lys Arg Leu Arg Gly
            500                 505                 510

Gly Val Arg Phe Leu Asp Glu Ile Pro Lys Gly Ser Thr Gly Lys Ile
        515                 520                 525

Asp Thr Thr Ala Leu Lys Gln Ile Leu Gln Lys Pro Asn Cys Lys Leu
530                 535                 540

<210> SEQ ID NO 2
<211> LENGTH: 1635
<212> TYPE: DNA
<213> ORGANISM: Luciola sp2

<400> SEQUENCE: 2
atgaacaaga acatcattta cggtccacca cccgtttatc ctcttgacga tggaacaggt      60
ggcgagcaat tgtacaaatg catttttaagg tacgccaaaa ttcctgaatg cgttgctttg    120
acaagcgcgc atactaaaga aagcatttta tacgaagaat tattgcaatt aacgtgcaaa    180
ttagctcaaa gcctaaagcg atgcggaatt acaagaaata gtactatcgc tgtgtgcagt    240
gaaaacaatc tgcaatactt tatacccatt atcgccggct atacattgg agctgccaca     300 gcagctgtta ataacagata caacgaacga gaacttaccg atattttaaa tttgtcaaaa    360
ccggatataa ttttttgctc taagaaaaca ttgccaaaaa tttgtcaagt caaaagaaa     420 ctgaattaca ttaagaaat tattgttctc gatagcaaac acgatagtga gttggctcaa    480
tgtttagata atttatttc ccacaattgc aacaaagatt tcgatgcgta tcagtttaag    540
ccaagctctt ttaaccgtaa cgagcaagta ggtttaatac taaattcgtc aggatcgaca    600
ggtcttccga aaggtgtaat gctaacgcat aaaaacttag tcgtgcgatt ttctcattgc    660
aaagatcccg ttttggtaa cataattct ccgggtactg ccatttta ac agttataccg    720 tttcaccatg gttttggtat gtttacaact ttggggtatt ttacatgtgg atttcgaatt    780
```

```
gttttaatgc acacgtttta cgaaaagttg tttttgcaag cgctagaaga ttataaagtt      840
gaaagtactt tattggtacc tactttaatg acgtttttg caaaaagcgc tttagtagat       900
aaatacaatt tgccgtattt aaggaaatt gcatcgggtg gtgccccgct atctaaagaa        960
atcggcgaag cagtagcacg aaggtttaaa ctaaacgcaa ttagacaagg ttatggttta     1020
actgaaacta catctgctgt attaattaca ccagaaagtg aaacagtacc tggatccata     1080
ggaaaggtgg tgccatttt cgcggctaaa ataattgatc atcgaactgg taaagcatta      1140
ggaccgaacg aagttggaga attatgtttt aaggggata tgattatgaa aggttactgt       1200
aataatattg aagcaactaa tgctataatc gacaacgacg ggtggctcca ttcgggcgat     1260
cttgggtatt acaacgacga taaacatttt ttcatagtag atcgacttaa gtctataata     1320
aaatacaaag atatcaagt cgctcctgct gaattagaag gtatattgtt aactcatcca      1380
agtattatgg acgctggtgt aactggtata cccgatgaca acgccggaga actaccagca     1440
gcatgtgttg tggttaaacc aggacggcat cttacagaag aaaatgtcat aaattacgta     1500
tcgagtcaag tgtcatccgt aaagagatta cgcggcggtg tgcgcttcct cgatgaaatt     1560
cccaaaggat ccacaggaaa aatcgatact acagctttga acaaattct gcaaaaaccg       1620 aactgcaaat tataa                                                                      1635

<210> SEQ ID NO 3
<211> LENGTH: 1635
<212> TYPE: DNA
<213> ORGANISM: Luciola sp2

<400> SEQUENCE: 3
atgaacaaga acatcattta cggtccacca cccgtttatc ctcttgacga tggaacaggt       60
ggcgagcaat tgtacaaatg cattttaagg tacgccaaaa ttcctgaatg cgttgctctg      120
acaagcgcgc atactaaaga aagcatttta tacgaagaat tattgcaatt aacgtgcaaa      180
ttagctcaaa gcctaaagcg atgcggaatt acaagaaata gtactatcgc tgtgtgcagt     240
gaaaacaatc tgcaatactt tatacccatt atcgccggct tatacattgg agctgccaca     300
gcagctgtta ataacagata caacgaacga gaacttaccg atattttaaa tttgtcaaaa     360
ccggatataa tttttttgctc taaagaaaca ttgccaaaaa tttgtcaagt caaaaagaaa    420
ctgaattaca ttaaagaaat tattgttctc gatagcaaac acgatagtga gttggctcaa    480
tgtttagata tttttatttc ccacaattgc aacaaagatt tcgatgcgta tcagtttaag     540
ccaagctctt ttaaccgtaa cgagcaagta ggtttaatac taaattcgtc aggatcgaca     600
ggtcttccga aggtgtaat gctaacgcat aaaaacttag tcgtgcgatt ttctcattgc      660
aaagatcccg ttttggtaa cataatttct ccgggtactg ccattttaac agttataccg       720
tttcaccatg gttttggtat gtttacaact ttggggtatt ttacatgtgg atttcgaatt     780
gttttaatgc acacgtttta cgaaaagttg tttttgcaag cgctagaaga ttataaagtt      840
gaaagtactt tattggtacc tactttaatg acgtttttg caaaaagcgc tttagtagat       900
aaatacaatt tgccgtattt aaggaaatt gcatcgggtg gtgccccgct atctaaagaa        960
atcggcgaag cagtagcacg aaggtttaaa ctaaacgcaa ttagacaagg ttatggttta     1020
actgaaacta catctgctgt attaattaca ccagaaagtg aaacagtacc tggttccata     1080
ggaaaggtgg tgccatttt cgcggctaaa ataattgatc atcgaactgg taaagcatta      1140
ggaccgaacg aagttggaga attatgtttt aaggggata tgattatgaa aggttactgt       1200
```

| | |
|---|---|
| aataatattg aagcaactaa tgctataatc gacaacgacg ggtggctcca ttcgggcgat | 1260 |
| cttgggtatt acaacgacga taaacatttt ttcatagtag atcgacttaa gtctataata | 1320 |
| aaatacaaag gatatcaagt cgctcctgct gaattagaag gtatattgtt aactcatcca | 1380 |
| agtattatgg acgctggtgt aactggtata cccgatgaca cgccggaga actaccagca | 1440 |
| gcatgtgttg tggttaaacc aggacggcat cttacagaag aaaatgtcat aaattacgta | 1500 |
| tcgagtcaag tgtcatccgt aaagagatta cgcggcggtg tgcgcttcct cgatgaaatt | 1560 |
| cccaaaggtt ccacaggaaa aatcgatact acagctttga acaaattct gcaaaaccg | 1620 |
| aactgcaaat tataa | 1635 |

<210> SEQ ID NO 4
<211> LENGTH: 1635
<212> TYPE: DNA
<213> ORGANISM: Luciola sp2

<400> SEQUENCE: 4

| | |
|---|---|
| atgaacaaga acatcatcta cggccctccc cccgtgtacc ccctggatga tggcacaggc | 60 |
| ggcgagcagc tgtacaagtg catcctgaga tacgccaaga tccccgagtg cgtggccctg | 120 |
| accagcgccc acaccaaaga gagcatcctg tacgaggaac tgctgcagct gacctgcaag | 180 |
| ctggcccaga gcctgaagag atgcggcatc acccggaaca gcacaatcgc cgtgtgcagc | 240 |
| gagaacaacc tgcagtactt catccccatc attgccggcc tgtacatcgg agccgccaca | 300 |
| gccgccgtga caaccggta caacgagaga gagctgaccg acatcctgaa cctgagcaag | 360 |
| cccgacatca tcttttgctc caagagaca ctgcccaaga tctgccaggt caagaagaag | 420 |
| ctgaactaca tcaaagaaat catcgtgctg gacagcaagc acgacagcga gctggctcag | 480 |
| tgtctggaca cttcatcag ccacaactgc aacaaggact tcgacgccta ccagttcaag | 540 |
| cccagcagct tcaaccggaa cgaacaggtc ggcctgatcc tgaacagcag cggcagcacc | 600 |
| ggcctgccca agggcgtgat gctgacccac aagaacctgg tggtgcgctt cagccactgc | 660 |
| aaggaccccg tgttcggcaa catcatcagc cccggcaccg ccatcctgac cgtgatccct | 720 |
| ttccaccacg gcttcggcat gttcaccacc ctgggctact tcacctgtgg cttccggatc | 780 |
| gtgctgatgc acaccttcta cgagaagctg ttcctgcagg ccctggaaga ttacaaggtg | 840 |
| gaaagcaccc tgctggtgcc tacccctgatg accttcttcg ccaagagcgc cctggtggac | 900 |
| aagtacaacc tgccctacct gaaagagatc gccagcggcg gagccccccct gagcaaagaa | 960 |
| atcggcgagg ccgtggccag acggttcaag ctgaacgcca tccggcaggg ctacggcctg | 1020 |
| accgagacaa ccagcgccgt gctgatcacc cccgagagcg agacagtgcc cggcagcatc | 1080 |
| ggcaaggtgg tgccattctt cgccgccaag atcatcgacc accggaccgg caaggccctg | 1140 |
| ggccctaatg aagtgggcga gctgtgcttc aagggcgaca tgatcatgaa gggctactgc | 1200 |
| aacaacatcg aggccaccaa cgccatcatc gacaacgacg gctggctgca cagcggcgat | 1260 |
| ctgggctact acaacgacga caagcacttc ttcatcgtgg accggctgaa gtccatcatc | 1320 |
| aagtacaagg gctaccaggt ggcccctgcc gagctggaag gcatcctgct gacacacccc | 1380 |
| agcatcatgg atgccggcgt gaccggcatc ccgacgata atgccggcga gctgcctgcc | 1440 |
| gcctgcgtgg tggtgaaacc cggcagacac ctgaccgagg aaaacgtgat caactacgtg | 1500 |
| tccagccagg tgtccagcgt gaagcggctg agaggcggcg tgcggttcct ggacgagatc | 1560 |
| cctaagggct ccaccggcaa gatcgacacc accgccctga agcagatcct gcagaagccc | 1620 |
| aactgcaagc tgtga | 1635 |

```
<210> SEQ ID NO 5
<211> LENGTH: 10
<212> TYPE: DNA
<213> ORGANISM: Artificial
<220> FEATURE:
<223> OTHER INFORMATION: Kozak sequence

<400> SEQUENCE: 5 gccrccatgg                                                                 10

<210> SEQ ID NO 6
<211> LENGTH: 9
<212> TYPE: PRT
<213> ORGANISM: Artificial
<220> FEATURE:
<223> OTHER INFORMATION: Conserved sequence

<400> SEQUENCE: 6

Leu Ile Lys Tyr Lys Gly Tyr Gln Val
1               5

<210> SEQ ID NO 7
<211> LENGTH: 23
<212> TYPE: DNA
<213> ORGANISM: Artificial
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 7
acytgrtanc cyttatattt aat                                                  23

<210> SEQ ID NO 8
<211> LENGTH: 23
<212> TYPE: DNA
<213> ORGANISM: Artificial
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 8
acytgrtanc cyttatattt gat                                                  23

<210> SEQ ID NO 9
<211> LENGTH: 23
<212> TYPE: DNA
<213> ORGANISM: Artificial
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 9
acytgrtanc cyttatattt tat                                                  23

<210> SEQ ID NO 10
<211> LENGTH: 23
<212> TYPE: DNA
<213> ORGANISM: Artificial
```

```
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 10
acytgrtanc cyttatactt aat                                            23

<210> SEQ ID NO 11
<211> LENGTH: 23
<212> TYPE: DNA
<213> ORGANISM: Artificial
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 11
acytgrtanc cyttatactt gat                                            23

<210> SEQ ID NO 12
<211> LENGTH: 23
<212> TYPE: DNA
<213> ORGANISM: Artificial
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 12
acytgrtanc cyttatactt tat                                            23

<210> SEQ ID NO 13
<211> LENGTH: 23
<212> TYPE: DNA
<213> ORGANISM: Artificial
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 13
acytgrtanc cyttgtattt aat                                            23

<210> SEQ ID NO 14
<211> LENGTH: 23
<212> TYPE: DNA
<213> ORGANISM: Artificial
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 14
acytgrtanc cyttgtattt gat                                            23

<210> SEQ ID NO 15
<211> LENGTH: 23
<212> TYPE: DNA
```

```
<213> ORGANISM: Artificial
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 15
acytgrtanc cyttgtattt tat                                           23

<210> SEQ ID NO 16
<211> LENGTH: 23
<212> TYPE: DNA
<213> ORGANISM: Artificial
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 16
acytgrtanc cyttgtactt aat                                           23

<210> SEQ ID NO 17
<211> LENGTH: 23
<212> TYPE: DNA
<213> ORGANISM: Artificial
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 17
acytgrtanc cyttgtactt gat                                           23

<210> SEQ ID NO 18
<211> LENGTH: 23
<212> TYPE: DNA
<213> ORGANISM: Artificial
<220> FEATURE:
<223> OTHER INFORMATION: 5' Race PCR Primer
<220> FEATURE:
<221> NAME/KEY: misc_feature
<222> LOCATION: (9)..(9)
<223> OTHER INFORMATION: n is a, c, g, or t

<400> SEQUENCE: 18
acytgrtanc cyttgtactt tat                                           23

<210> SEQ ID NO 19
<211> LENGTH: 23
<212> TYPE: DNA
<213> ORGANISM: Artificial
<220> FEATURE:
<223> OTHER INFORMATION: Gene Racer 5' Primer

<400> SEQUENCE: 19
cgactggagc acgaggacac tga                                           23

<210> SEQ ID NO 20
<211> LENGTH: 26
<212> TYPE: DNA
<213> ORGANISM: Artificial
<220> FEATURE:
<223> OTHER INFORMATION: Gene Racer 5' Nested Primer
```

<400> SEQUENCE: 20
ggacactgac atggactgaa ggagta      26

<210> SEQ ID NO 21
<211> LENGTH: 19
<212> TYPE: DNA
<213> ORGANISM: Artificial
<220> FEATURE:
<223> OTHER INFORMATION: Primer for colony PCR

<400> SEQUENCE: 21
cacgacgttg taaaacgac      19

<210> SEQ ID NO 22
<211> LENGTH: 18
<212> TYPE: DNA
<213> ORGANISM: Artificial
<220> FEATURE:
<223> OTHER INFORMATION: Primer for colony PCR

<400> SEQUENCE: 22
ggataacaat ttcacagg      18

<210> SEQ ID NO 23
<211> LENGTH: 1349
<212> TYPE: DNA
<213> ORGANISM: Luciola sp2

<400> SEQUENCE: 23

| | |
|---|---|
| aactctatca tgaacaagaa catcatttac ggtccaccac ccgtttatcc tcttgacgat | 60 |
| ggaacaggtg cgagcaatt gtacaaatgc atttttaaggt acgccaaaat tcctgaatgc | 120 |
| gttgctttga caagcgcgca tactaaagaa agcatttttat acgaagaatt attgcaatta | 180 |
| acgtgcaaat tagctcaaag cctaaagcga tgcggaatta caagaaatag tactatcgct | 240 |
| gtgtgcagtg aaaacaatct gcaatacttt atacccatta tcgccggctt atacattgga | 300 |
| gctgccacag cagctgttaa taacagatac aacgaacgag aacttaccga tattttaaat | 360 |
| ttgtcaaaac cggatataat tttttgctct aaagaaacat tgccaaaaat ttgtcaagtc | 420 |
| aaaaagaaac tgaattacat taagaaaatt attgttctcg atagcaaaca cgatagtgag | 480 |
| ttggctcaat gtttagataa ttttatttcc cacaattgca acaaagattt cgatgcgtat | 540 |
| cagtttaagc caagctcttt taaccgtaac gagcaagtag gtttaatact aaattcgtca | 600 |
| ggatcgacag gtcttccgaa aggggtaatg ctaacgcata aaaacttagt cgtgcgattt | 660 |
| tctcattgca aagatcccgt ttttggtaac ataatttytc cgggtactgc catttttaaca | 720 |
| gttataccgt ttcaccacgg ttttggtatg tttacgactt tgggatattt tacatgtgga | 780 |
| tttcggattg ttttaatgca cacgttttac gaacagttgt ttttgcaagc gctagaagat | 840 |
| tataaagttg aaagtacttt attggtacct actttaatga cgtttttgc aaaaagcgct | 900 |
| ttagtagata aatacaattt gccgtattta aggaaattg catcgggtgg tgccccacta | 960 |
| tctaaagaaa tcggcgaagc agtagcacga aggtttaaat taaacgcaat tagacaaggt | 1020 |
| tatggtttaa ctgaaactac atctgctgta ttaattacac cagaaagtga aacagtacct | 1080 |
| ggatccatag gaaaggtggt gccatttttc gcggctaaaa taattgaaca tcaaactggt | 1140 |
| aaagcattag gaccgaacga agttggagaa ttatgtttta aggggaaat gattatgaaa | 1200 |
| ggttactgta ataatattga agcaacaaat gctataatcg acaacgacgg gtggctccat | 1260 |

```
tcgggcgatc ttgggtatta caacgacgat aaacattttt tcatcgtaga tcgacttaag    1320
tctataataa agtacaaagg ctaccaggt                                      1349
```

<210> SEQ ID NO 24
<211> LENGTH: 30
<212> TYPE: DNA
<213> ORGANISM: Artificial
<220> FEATURE:
<223> OTHER INFORMATION: Primer for full length cloning

<400> SEQUENCE: 24

```
aactctatca tgaacaagaa catcatttac                                     30
```

<210> SEQ ID NO 25
<211> LENGTH: 36
<212> TYPE: DNA
<213> ORGANISM: Artificial
<220> FEATURE:
<223> OTHER INFORMATION: Primer for full length cloning

<400> SEQUENCE: 25

```
aactctatca tgaacaagaa catcatttac ggtcca                              36
```

<210> SEQ ID NO 26
<211> LENGTH: 25
<212> TYPE: DNA
<213> ORGANISM: Artificial
<220> FEATURE:
<223> OTHER INFORMATION: Gene Racer 3' Primer

<400> SEQUENCE: 26

```
gctgtcaacg atacgctacg taacg                                          25
```

<210> SEQ ID NO 27
<211> LENGTH: 23
<212> TYPE: DNA
<213> ORGANISM: Artificial
<220> FEATURE:
<223> OTHER INFORMATION: Gene Racer 3' Nested Primer

<400> SEQUENCE: 27

```
cgctacgtaa cggcatgaca gtg                                            23
```

<210> SEQ ID NO 28
<211> LENGTH: 20
<212> TYPE: DNA
<213> ORGANISM: Artificial
<220> FEATURE:
<223> OTHER INFORMATION: T7 Promoter Primer

<400> SEQUENCE: 28

```
taatacgact cactataggg                                                20
```

<210> SEQ ID NO 29
<211> LENGTH: 21
<212> TYPE: DNA
<213> ORGANISM: Artificial
<220> FEATURE:
<223> OTHER INFORMATION: T7 Reverse Primer

<400> SEQUENCE: 29

```
ctagttattg ctcagcggtg g                                              21
```

<210> SEQ ID NO 30
<211> LENGTH: 544

<212> TYPE: PRT
<213> ORGANISM: Luciola sp2

<400> SEQUENCE: 30

```
Met Asp Lys Asn Ile Ile Tyr Gly Pro Pro Val Tyr Pro Leu Asp
1               5                   10                  15

Asp Gly Thr Gly Gly Glu Gln Leu Tyr Lys Cys Ile Leu Arg Tyr Ala
            20                  25                  30

Lys Ile Pro Glu Cys Val Ala Leu Thr Ser Ala His Thr Lys Glu Ser
            35                  40                  45

Ile Leu Tyr Glu Glu Leu Leu Gln Leu Thr Cys Lys Leu Ala Gln Ser
        50                  55                  60

Leu Lys Arg Cys Gly Ile Thr Arg Asn Ser Thr Ile Ala Val Cys Ser
65                  70                  75                  80

Glu Asn Asn Leu Gln Tyr Phe Ile Pro Ile Ile Ala Gly Leu Tyr Ile
                85                  90                  95

Gly Ala Ala Thr Ala Ala Val Asn Asn Arg Tyr Asn Glu Arg Glu Leu
            100                 105                 110

Thr Asp Ile Leu Asn Leu Ser Lys Pro Asp Ile Ile Phe Cys Ser Lys
        115                 120                 125

Glu Thr Leu Pro Lys Ile Cys Gln Val Lys Lys Leu Asn Tyr Ile
        130                 135                 140

Lys Glu Ile Ile Val Leu Asp Ser Lys His Asp Ser Glu Leu Ala Gln
145                 150                 155                 160

Cys Leu Asp Asn Phe Ile Ser His Asn Cys Asn Lys Asp Phe Asp Ala
                165                 170                 175

Tyr Gln Phe Lys Pro Ser Ser Phe Asn Arg Asn Glu Gln Val Gly Leu
            180                 185                 190

Ile Leu Asn Ser Ser Gly Ser Thr Gly Leu Pro Lys Gly Val Met Leu
        195                 200                 205

Thr His Lys Asn Leu Val Val Arg Phe Ser His Cys Lys Asp Pro Val
    210                 215                 220

Phe Gly Asn Ile Ile Ser Pro Gly Thr Ala Ile Leu Thr Val Ile Pro
225                 230                 235                 240

Phe His His Gly Phe Gly Met Phe Thr Thr Leu Gly Tyr Phe Thr Cys
                245                 250                 255

Gly Phe Arg Ile Val Leu Met His Thr Phe Tyr Glu Lys Leu Phe Leu
            260                 265                 270

Gln Ala Leu Glu Asp Tyr Lys Val Glu Ser Thr Leu Leu Val Pro Thr
        275                 280                 285

Leu Met Thr Phe Phe Ala Lys Ser Ala Leu Val Asp Lys Tyr Asn Leu
    290                 295                 300

Pro Tyr Leu Lys Glu Ile Ala Ser Gly Gly Ala Pro Leu Ser Lys Glu
305                 310                 315                 320

Ile Gly Glu Ala Val Ala Arg Arg Phe Lys Leu Asn Ala Ile Arg Gln
                325                 330                 335

Gly Tyr Gly Leu Thr Glu Thr Thr Ser Ala Val Leu Ile Thr Pro Glu
            340                 345                 350

Ser Glu Thr Val Pro Gly Ser Ile Gly Lys Val Val Pro Phe Phe Ala
        355                 360                 365

Ala Lys Ile Ile Asp His Arg Thr Gly Lys Ala Leu Gly Pro Asn Glu
    370                 375                 380

Val Gly Glu Leu Cys Phe Lys Gly Asp Met Ile Met Lys Gly Tyr Cys
385                 390                 395                 400
```

Asn Asn Ile Glu Ala Thr Asn Ala Ile Ile Asp Asn Asp Gly Trp Leu
            405                 410                 415

His Ser Gly Asp Leu Gly Tyr Tyr Asn Asp Asp Lys His Phe Phe Ile
        420                 425                 430

Val Asp Arg Leu Lys Ser Ile Ile Lys Tyr Lys Gly Tyr Gln Val Ala
            435                 440                 445

Pro Ala Glu Leu Glu Gly Ile Leu Leu Thr His Pro Ser Ile Met Asp
        450                 455                 460

Ala Gly Val Thr Gly Ile Pro Asp Asp Asn Ala Gly Glu Leu Pro Ala
465                 470                 475                 480

Ala Cys Val Val Val Lys Pro Gly Arg His Leu Thr Glu Glu Asn Val
                485                 490                 495

Ile Asn Tyr Val Ser Ser Gln Val Ser Ser Val Lys Arg Leu Arg Gly
            500                 505                 510

Gly Val Arg Phe Leu Asp Glu Ile Pro Lys Gly Ser Thr Gly Lys Ile
        515                 520                 525

Asp Thr Thr Ala Leu Lys Gln Ile Leu Gln Lys Pro Asn Cys Lys Leu
    530                 535                 540

<210> SEQ ID NO 31
<211> LENGTH: 1635
<212> TYPE: DNA
<213> ORGANISM: Luciola sp2

<400> SEQUENCE: 31

```
atggacaaga acatcatcta cggccctccc ccgtgtacc  ccctggatga tggcacaggc      60
ggcgagcagc tgtacaagtg catcctgaga tacgccaaga tccccgagtg cgtggccctg     120
accagcgccc acaccaaaga gagcatcctg tacgaggaac tgctgcagct gacctgcaag     180
ctggcccaga gcctgaagag atgcggcatc acccggaaca gcacaatcgc cgtgtgcagc     240
gagaacaacc tgcagtactt catccccatc attgccggcc tgtacatcgg agccgccaca     300
gccgccgtga caaccggta caacgagaga gagctgaccg acatcctgaa cctgagcaag     360
cccgacatca tcttttgctc caagagaca ctgcccaaga tctgccaggt caagaagaag     420
ctgaactaca tcaaagaaat catcgtgctg acagcaagc acgacagcga gctggctcag     480
tgtctggaca cttcatcag ccacaactgc aacaaggact cgacgcccta ccagttcaag     540
cccagcagct tcaaccggaa cgaacaggtc ggcctgatcc tgaacagcag cggcagcacc     600
ggcctgccca gggcgtgat gctgacccac aagaacctgg tggtgcgctt cagccactgc     660
aaggaccccg tgttcggcaa catcatcagc cccggcaccg ccatcctgac cgtgatccct     720
ttccaccacg gcttcggcat gttcaccacc ctgggctact tcacctgtgg cttccggatc     780
gtgctgatgc acaccttcta cgagaagctg ttcctgcagg ccctggaaga ttacaaggtg     840
gaaagcaccc tgctggtgcc taccctgatg accttcttcg ccaagagcgc cctggtggac     900
aagtacaacc tgccctacct gaaagagatc gccagcggcg agcccccct gagcaaagaa     960 atcggcgagg ccgtggccag acggttcaag ctgaacgcca tccggcaggg ctacggcctg    1020
accgagacaa ccagcgccgt gctgatcacc cccgagagcg agacagtgcc cggcagcatc    1080
ggcaaggtgg tgccattctt cgccgccaag atcatcgacc accggaccgg caaggccctg    1140
ggccctaatg aagtgggcga gctgtgcttc aagggcgaca tgatcatgaa gggctactgc    1200
aacaacatcg aggccaccaa cgccatcatc gacaacgacg ctggctgca cagcggcgat    1260 ctgggctact acaacgacga caagcacttc ttcatcgtgg accggctgaa gtccatcatc    1320
```

```
aagtacaagg gctaccaggt ggcccctgcc gagctggaag gcatcctgct gacacacccc    1380
agcatcatgg atgccggcgt gaccggcatc cccgacgata atgccggcga gctgcctgcc    1440
gcctgcgtgg tggtgaaacc cggcagacac ctgaccgagg aaaacgtgat caactacgtg    1500
tccagccagg tgtccagcgt gaagcggctg agaggcggcg tgcggttcct ggacgagatc    1560
cctaagggct ccaccggcaa gatcgacacc accgccctga agcagatcct gcagaagccc    1620
aactgcaagc tgtga                                                    1635
```